(12) United States Patent
Sakaguchi et al.

(10) Patent No.: US 7,914,830 B2
(45) Date of Patent: *Mar. 29, 2011

(54) COMPOSITION FOR INHIBITING THROMBOSIS

(75) Inventors: Noboru Sakaguchi, Yokkaichi (JP); Hidetoshi Sugino, Yokkaichi (JP); Tsutomu Okubo, Yokkaichi (JP); Toshihiro Ito, Yokkaichi (JP); Tomohiko Kihira, Yokkaichi (JP); Seon-Joo Yoon, Youngcheon-si (KR); Theertham Pradyumna Rao, Yokkaichi (JP); Htay Hlahla, Yokkaichi (JP); Lekh Raj Juneja, Yokkaichi (JP)

(73) Assignee: Taiyo Kagaku Co., Ltd, Yokkaichi-Shi, Mie (JP)

( * ) Notice: Subject to any disclaimer, the term of this patent is extended or adjusted under 35 U.S.C. 154(b) by 1046 days.

This patent is subject to a terminal disclaimer.

(21) Appl. No.: 10/581,287

(22) PCT Filed: Nov. 30, 2004

(86) PCT No.: PCT/JP2004/017780
§ 371 (c)(1),
(2), (4) Date: Feb. 6, 2007

(87) PCT Pub. No.: WO2005/058339
PCT Pub. Date: Jun. 30, 2005

(65) Prior Publication Data
US 2008/0317774 A1    Dec. 25, 2008

(30) Foreign Application Priority Data

| Dec. 4, 2003 | (JP) | 2003-405436 |
|---|---|---|
| Dec. 4, 2003 | (JP) | 2003-405449 |
| Dec. 4, 2003 | (JP) | 2003-405452 |
| Dec. 19, 2003 | (JP) | 2003-421762 |
| Dec. 19, 2003 | (JP) | 2003-421765 |
| Dec. 19, 2003 | (JP) | 2003-421803 |
| Jun. 22, 2004 | (JP) | 2004-183472 |
| Sep. 21, 2004 | (JP) | 2004-273336 |
| Sep. 21, 2004 | (JP) | 2004-273361 |
| Nov. 12, 2004 | (JP) | 2004-328521 |
| Nov. 12, 2004 | (JP) | 2004-328522 |
| Nov. 12, 2004 | (JP) | 2004-328526 |
| Nov. 12, 2004 | (JP) | 2004-328529 |
| Nov. 12, 2004 | (JP) | 2004-328531 |
| Nov. 12, 2004 | (JP) | 2004-328534 |
| Nov. 12, 2004 | (JP) | 2004-328536 |

(51) Int. Cl.
*A61K 36/00* (2006.01)

(52) U.S. Cl. ........ 424/777; 424/725

(58) Field of Classification Search .......... None
See application file for complete search history.

(56) References Cited

U.S. PATENT DOCUMENTS

| 6,290,996 B1 | 9/2001 | Ghosal et al. |
|---|---|---|
| 6,776,979 B2 * | 8/2004 | Frager et al. ........ 424/50 |

FOREIGN PATENT DOCUMENTS

| CN | 1278433 A | | 1/2001 |
|---|---|---|---|
| CN | 1278433 A | * | 1/2001 |
| JP | 2002-171934 A | | 6/2002 |
| JP | 2003-171294 A | | 6/2003 |
| JP | 2004-065047 A | | 3/2004 |

OTHER PUBLICATIONS

Bordia A. et al., Indian Heart Journal, 1985, vol. 37, No. 3, pp. 179 to 182.

Rao, Asia Pacific J Clin Nutr., 2003, vol. 12., No. 1, pp. 9-22 and pp. 1 and 2 of 13, XP-002441858.

* cited by examiner

*Primary Examiner* — Susan C Hoffman

(74) *Attorney, Agent, or Firm* — Birch, Stewart, Kolasch & Birch, LLP

(57) ABSTRACT

The present invention provides a composition for inhibiting thrombus formation, comprising a given plant component derived from amla, tea, *hibiscus*, cocklebur, *gymnema*, *Hizikia fusiforme* or carrageenan, which can be used for foodstuff, quasi-drugs, medicaments and feeds.

14 Claims, No Drawings

COMPOSITION FOR INHIBITING THROMBOSIS

TECHNICAL FIELD

The present invention relates to a composition for inhibiting thrombus formation.

BACKGROUND ART

Thrombus refers to a blood clot generated in a blood vessel, in which a protein called fibrinogen is activated, and forms into an insoluble polymer together with platelets, leukocytes and the like while being converted into fibrin, which is solidified on an inner wall of a blood vessel resulting in thrombus. When a body is normal, plasmin functioning to lyse fibrin, a causation for this thrombus, prevents thrombus. However, when plasmin is deficient, fibrin cannot be lysed, whereby thrombus is generated. There are primary hemostasis (platelet aggregation) and secondary hemostasis (blood coagulation) in thrombus. Bleeding is generated by damage of a blood vessel, and platelets are adhered to and aggregated to a hole perforated on a blood vessel wall, thereby temporarily arresting the hemorrhage. This is referred to as primary hemostasis, and the generated thrombus is referred to as primary thrombus. Further, a water-soluble coagulation factor (fibrinogen) in the plasma becomes water-insoluble (fibrin), a net is formed between platelets in a thread-like manner, thereby reinforcing primary thrombus. This is referred to as secondary hemostasis, and generated thrombus is referred to as secondary thrombus.

Platelet aggregation is generated by exposing collagen in a wall by damage of a blood vessel wall, adhering a platelet to exposed collagen, and further aggregating platelets to each other. Mechanism of blood coagulation includes intrinsic blood coagulation and extrinsic blood coagulation. In the intrinsic blood coagulation, a factor XII is contacted with a subendothelial tissue having a negative charge to activate the factor XII, a factor XI is then activated by the activated factor XII, the intrinsic blood coagulation factors being sequentially activated, and finally, fibrinogen, a factor I is subjected to limited degradation by thrombin, an active form of a factor II (prothrombin) to form fibrin, whereby thrombus is formed. The extrinsic blood coagulation is activated by tissue factor and a factor VII, and coagulation progresses from activation of a factor X towards coagulation mechanism common with the intrinsic blood mechanism. Finally, fibrinogen, the factor I is subjected to limited degradation by thrombin, an active form of the factor II (prothrombin) to form fibrin, whereby thrombus is formed.

The formed thrombus is deposited in a blood vessel to reduce a cross-sectional area of a blood vessel, thereby inhibiting the circulation of blood. As a result, there arise some problems that the blood cannot normally supply nutrients and oxygen to cells and tissues, so that waste substances of the cells and the tissues cannot be excreted, whereby toxicity is accumulated, and the like.

Symptom caused by thrombus in a blood vessel is called thrombosis in a broad sense (hereinafter, when simply described as "thrombosis," this refers to thrombosis in a broad sense), and pathological conditions caused by thrombus are classified into thrombosis in a narrow sense and embolism. Thrombosis in a narrow sense is symptom due to partial or complete occlusion of a blood stream by thrombus at a site where thrombus is formed, and embolism refers to a pathological condition caused by peeling of thrombus from a site where it is formed, movement of thrombus through a blood stream, and partial or complete occlusion of a blood stream by the thrombus at other sites.

The thrombosis as described above is likely to induce a variety of diseases depending upon a site of a blood vessel where thrombus is generated. Among them, particularly, when thrombus is generated in a cerebral blood vessel or a cardiac blood vessel, a serious symptom such as stroke, cerebral hemorrhage, cerebral infarction, cardiac failure, cardiac infarction or cardiac paralysis is generated, thereby causing hemiplegia, or death in a severe case.

Serious thrombus causing these cardiac diseases, cerebral blood vessel diseases and the like is different in mechanism from fibrin thrombus formed under retention of a blood stream. It is thought that the thrombus is formed in the presence of a relatively rapid and ample blood stream such as an artery. Under a blood stream, even when a coagulation factor is activated, since this is diluted with a blood stream, this efficiently does not lead to thrombus formation. However, platelet which is a component adhering to a damaged blood vessel wall, and aggregating to enhance a local concentration plays a more important role in the formation of thrombus.

When a vascular endothelial cell undergoes a disorder and is peeled, collagen of a vascular subendothelial cell tissue is exposed, and crosslinking is formed (adhered) between collagen and von-willebrand factor (vWF: VII factor) receptor (GpIb) by vWF synthesized in a vascular endothelial cell. Further, platelet is activated by an agonist such as thrombin, to be bound with other platelet by a fibrinogen receptor (GpIIb-IIIa) via fibrinogen, thereby causing platelet aggregation, whereby platelet thrombus is formed. Therefore, whether or not formation of cross-linking between collagen and GpIb by vWF, or binding with other platelet by GpIIb-IIIa via fibrinogen can be inhibited is one of important requirements for preventing thrombus formation.

As an agonist which promotes cross-linking formation between the collagen and GpIb by vWF, ristocetin has been known. As an agonist which promotes binding with other platelet by GpIIb-IIIa via fibrinogen, adenosine diphosphate (ADENOSINE 5'DIPHOSPHATE SODIUM: ADP) released from vascular platelet and damaged hemocyte, endothelium or tissue by various substances such as collagen and thrombin has been known.

In the treatment of thrombosis, an antithrombotic agent and a thrombus formation preventing agent for inhibiting formation of thrombus, and a thrombolytic agent for lysing generated thrombus have been mainly studied and developed.

The antithrombotic agent includes an anti-platelet agent and an anti-coagulant. The anti-platelet agent is purposed for inhibiting the function of platelet involved in an early stage of thrombus formation. Numerous orally administrable drugs such as aspirin have been developed, but these drugs have been currently used for preventing recurrence of cerebral infarct, cardiac infarct and the like, and preventing occlusion after various bypass operations. Therefore, these drugs have been used as a thrombus formation preventing drug rather than as a therapeutic agent for thrombosis. As the anti-coagulant, heparin which acts by promoting inhibition of thrombin due to antithrombin III, warfarin which is a coumarin derivative as an oral anti-coagulant have been and the like clinically used. Warfarin inhibits the generation of thrombin by inhibiting vitamin K-dependent γ-carboxylation after the translation in prothrombin synthesis. However, since heparin must be administered parenterally and heparin functions as a cofactor of antithrombin III, heparin has no effect without this inhibitor. Warfarin exhibits effects very slowly, and individual doses must be adjusted by frequent tests. Among these anti-coagulants, there is no anti-coagulant which is specific only for thrombin, and these anti-coagulants also inhibit other serine-protease; therefore, there is a possibility that bleeding is induced unless both doses are accurately adjusted. Recently, eicosapentaenoic acid (EPA), prostacycline (PG12) derivative and the like have also been merchandized. However, since these drugs have no specificity, they also affect on a part other than thrombus in a living body. Therefore, when these drugs remain in a living body, there is a possibility that bleeding or the like is caused. Besides, antithrombotic activity for hirudin, synthetic antithrombin, Ticlopidin or the like has been also reported, but not yet put into practical use.

As the thrombolytic agent, a plasminogen activator such as streptokinase or urokinase has been known, and a therapeutic method of intravenously injecting a plasminogen activator to a patient with thrombus formed to activate a thrombolytic system in a body has been generally used. Although its thrombolytic effect has been verified in some clinical experiments, there is no specificity for thrombus in the same manner as in the antithrombotic agent or the thrombus formation preventing agent, and there is an adverse action such as systemic bleeding during treatment of thrombus. In addition, there has been thought that a tissue-type plasminogen activator (tPA) has high selectivity for thrombus, and is an ideal thrombolytic agent. However, as a result of actual application to clinical treatment, there was still an adverse action such as systemic bleeding with some differences in its extent. In addition, since a half-life in the blood is very short and a sustaining time for drug efficacy is short, a dose must be large in order to sustain the drug efficacy in a body. For this reason, there is a disadvantage that the therapeutic cost is very high as compared to a conventional thrombolytic agent.

Although the medicaments as mentioned above have been used for preventing generation of thrombus, the medicaments do not exhibit remarkable effects in thrombus removal, but induce serious adverse actions. Therefore, recently, studies on a component or a food component which has a function of preventing a disease, or regulating or activating physical condition thorough dietary life rather than a treatment with a medicament have been remarked.

As the food component, a material such as a polyvalent unsaturated fatty acid, glucosamine, or a thin skin of an onion (see, for instance, Patent Publication 1) has been known. However, there is a disadvantage in flavor, nature and the like, so that the material could not be widely applied to foods.

In addition, recently, a patent regarding a kiwi fruit extract (see, for instance, Patent Publication 2) has been published. However, there is a disadvantage that the extract has weak activity in a neutral range.

Further, nattokinase (see, for instance, Patent Publication 3) has been well known. However, although nattokinase has a thrombolytic effect, nattokinase contains vitamin K which contributes to the production of a coagulation factor, at the same time.

Patent Publication 1: Japanese Patent Laid-Open No. 2002-171934 (page 2)
Patent Publication 2: Japanese Patent Laid-Open No. 2003-171294 (pages 2-5)
Patent Publication 3: Japanese Patent Laid-Open No. 2004-65047 (page 3)

DISCLOSURE OF THE INVENTION

Problems to be Solved by the Invention

An object of the present invention is to provide a composition for inhibiting thrombus formation comprising a given plant component, which can be used for foodstuff, quasi-drugs, medicaments and feeds.

Means to Solve the Problems

The present inventors have studied multi-dimensionally for the purpose of finding a thrombus formation inhibitory component with utilizing various natural plants. Consequently, they have found that given plant components derived from amla, tea, *hibiscus*, cocklebur, *gymnema*, *Hizikia fusiforme* and carrageenan have excellent thrombus formation inhibitory activity. The present invention has been accomplished thereby.

Specifically, the gist of the present invention relates to:
[1] an antithrombotic composition characterized in that the composition comprises at least one member selected from the group consisting of fruit or fruit juice of amla and an extract thereof;
[2] a fibrin formation inhibitory composition characterized in that the composition comprises at least one member selected from the group consisting of fruit or fruit juice of amla and an extract thereof;
[3] an anti-platelet aggregation composition characterized in that the composition comprises at least one member selected from the group consisting of fruit or fruit juice of amla and an extract thereof;
[4] a platelet aggregation inhibitory composition characterized in that the composition comprises at least one member selected from the group consisting of fruit or fruit juice of amla and an extract thereof;
[5] a composition for anti-thrombus characterized in that the composition comprises an extract of tea;
[6] a composition for anti-platelet aggregation characterized in that the composition comprises an extract of tea;
[7] an anti-blood coagulant composition characterized in that the composition comprises at least one member selected from the group consisting of fruit, fruit juice or leaf of *hibiscus* and an extract thereof;
[8] a platelet aggregation preventing composition characterized in that the composition comprises at least one member selected from the group consisting of fruit, fruit juice or leaf of *hibiscus* and an extract thereof;
[9] a composition for preventing platelet aggregation characterized in that the composition comprises at least one member selected from the group consisting of fruit, fruit juice or leaf of *hibiscus* and an extract thereof;
[10] a platelet aggregation thrombus inhibitory composition characterized in that the composition comprises at least one member selected from the group consisting of fruit, fruit juice or seed of cocklebur and an extract thereof;
[11] a composition for inhibiting platelet aggregation thrombus characterized in that the composition comprises at least one member selected from the group consisting of fruit, fruit juice or seed of cocklebur and an extract thereof;
[12] a thrombus formation inhibitory agent characterized in that the agent comprises *gymnema*, an extract thereof or a mixture thereof;
[13] an extrinsic blood coagulation preventing composition characterized in that the composition comprises *Hizikia fusiforme*, an extract thereof or a mixture thereof;
[14] a thrombus preventing composition characterized in that the composition comprises *Hizikia fusiforme*, an extract thereof or a mixture thereof;
[15] a composition for preventing thrombus characterized in that the composition comprises an enzymatically treated product of *Hizikia fusiforme*, an extract thereof or a mixture thereof; and
[16] an antithrombotic agent characterized in that the agent comprises carrageenan.

Effects of the Invention

According to the present invention, there is provided a composition for inhibiting thrombus formation comprising the given plant component mentioned above having a thrombus formation inhibitory activity. The component is derived from a natural plant which has been previously used in a daily dietary life of human. Therefore, unlike the previous drugs, thrombus formation is inhibited safely without an adverse action of causing bleeding in a body, and cardiovascular diseases such as cerebral bleeding, cerebral infarct, cardiac infarct, arteriosclerosis and coronary arteriopathy can be prevented by using the composition. The composition for inhibiting thrombus formation of the present invention can be applied, for instance, to foodstuff, quasi-drugs, medicaments and feeds.

BEST MODE FOR CARRYING OUT THE INVENTION

The present invention overall provides a composition for inhibiting thrombus formation. More specifically, the present invention provides various compositions depending upon a plant component which is used as an effective ingredient. The composition of the present invention may be an effective ingredient as it is. The present invention will be explained for every plant which is used hereinbelow. The raw materials of the composition of the present invention and the like may be arbitrarily used alone, or in admixture of two or more kinds.

As used herein, the terms "anti-platelet aggregation," "platelet aggregation inhibition," "platelet aggregation prevention," and "anti-platelet" have a similar meaning.

(1) Amla

Specifically, the present invention provides an antithrombotic composition, a fibrin formation inhibitory composition, an anti-platelet aggregation composition, and a platelet aggregation inhibitory composition, characterized in that each composition comprises, as an effective ingredient, at least one member selected from the group consisting of fruit or fruit juice of amla and an extract thereof.

The composition of the present invention exhibits its effects based on the action owned by the above-mentioned amla component. The following action for the amla component has been found for the first time in the present invention.

Specifically, it was seen from the results of the measurement of an activated partial thromboplastin time (APTT) for the above-mentioned amla component that the effect of inactivating a factor involved in an intrinsic pathway to inhibit fibrin formation and inhibit formation of thrombus in a blood vessel is enhanced.

It was seen from the results of the fibrin formation inhibitory test for the above-mentioned amla component that the effect of inhibiting the formation of fibrin from fibrinogen due to thrombin at a final stage of thrombus formation is enhanced.

It was seen from the results of a platelet aggregation test for the above-mentioned amla component that the effect of inhibiting formation of a platelet aggregate is enhanced. Specifically, for the above-mentioned amla component, it was seen from the test results of platelet aggregation, caused when ADP, which is an agonist for inducing a stage of connecting with other platelet via fibrinogen by GpIIb-IIIa to cause platelet aggregation, is added, a so-called ADP-induced platelet aggregation, that an effect of inhibiting the platelet aggregation by inhibiting a binding step with other platelet by GpIIb-IIIa via fibrinogen is enhanced.

For the above-mentioned amla component, it was seen from the test results of platelet aggregation caused when ristocetin, which is an agonist for causing the platelet aggregation by cross-linking formation between collagen and GpIb by vWF, is added, a so-called ristocetin-induced platelet aggregation, that the effect of inhibiting cross-linking formation between collagen and GpIb by vWF is enhanced.

The amla used in the present invention has a scientific name of *Emblica officinale* or *Phyllanthus embilica*, and is a deciduous subarborous tree belonging to Euphorbiaceae Phyllanthus, and is distributed from the regions of India, Malaysian and Southern China, and India is thought to be the place of origin. In addition, the amla has endemic names respectively depending upon each region or language, and is also referred to as youganzi, yougan, Anmaroku, embolic myrobalan, himawarik, malaka, malaka tree, Indian gooseberry, Alonla, Amali, Amlaki, Amila chatra, Nellikayi, Nelli, Tasha, Kayruk, Kemurak, Mak kham pom, or the like.

In the present invention, fruit is preferably used as a part of the amla. Its form is not particularly limited, either of all or a part of immature fruit, fully mature fruit, dried fruit or the like may be used. In addition, fruit juice obtained by squeezing fruit is also used as an active ingredient. Fruit juice may be used in the form of a fruit juice powder or the like.

In the case of the fruit juice or fruit juice powder, it may be used as it is. However, when one containing a water-insoluble component such as raw fruit or dried fruit is used, it is preferable that the water-insoluble component is removed by extraction from the viewpoint of enhancement in effect.

When the raw fruit is used during the extraction, it is preferable that after removal of a seed, the raw fruit used as an extraction raw material is crushed and mixed thoroughly with a mixer or the like with or without the addition of water in order to enhance extraction efficacy.

When the dried fruit is used, it is preferable that the dried fruit used as an extraction raw material is pulverized to a particle size of 40 mesh or smaller in order to enhance extraction efficacy.

Alternatively, the fruit juice is also used as an extraction raw material.

It is preferable that an extract in the antithrombotic composition of the present invention is prepared as follows:

The extraction method is not particularly limited in an extraction solvent, an extraction temperature or the like. As the extraction solvent, a non-organic solvent such as water, a base, an acid or an aqueous sodium chloride solution can be used. Preferable is at least one member selected from the group consisting of water, bases and acids.

When the acid or base is used as the extraction solvent, it is preferable to neutralize an extract. A salt formed by a neutralization reaction can be removed by a known method such as a dialysis method or gel filtration. When water is used as the extraction solvent, since the neutralization reaction as mentioned above is not necessary, and removal of the formed salt is not necessitated, it is further preferable to use water.

The acid to be used in the extraction method is not particularly limited, and most of acids can be used. Preferable is use of one kind selected from hydrochloric acid and sulfuric acid, or a combination of both.

In addition, the base is not particularly limited, and most of bases can be used. Preferable is use of one kind selected from sodium hydroxide and potassium hydroxide, or a combined use of both.

The concentration of the acid or base to be used in the extraction is not particularly limited, and varies depending upon the intensity of the acid or base, and is preferably a concentration of from 0.01 to 0.5 molar. Usually, the acid or base is used as an aqueous solution having the above concentration.

The extraction solvent may be used preferably in an amount of from 500 to 5000 parts by weight based on 100 parts by weight of the dried extraction raw material. An extraction temperature is suitably from 40° to 70° C. The extraction may be carried out by allowing the mixture to stand or while stirring.

The drying procedure as used herein can be carried out by keeping an object to be dried at a temperature of from 60° to 110° C. for 2 to 16 hours in a drier [for instance, a blast constant temperature drier (manufactured by Yamato)]. For instance, an object to be dried is dried by keeping at a temperature of 70° C. for 10 hours.

In the above-mentioned extraction, it is preferable that an extraction efficiency is improved by repeating an extraction step again one or more times on the extraction residue, and that its yield is improved. The solvent used for extraction in this case may be the same, or different solvents may be used.

The fruit juice or the extract (extract-containing solution, hereinafter referred to the same) obtained as described above may be used as it is. It is preferable that insoluble substances are removed by filtration or centrifugation, whereby the antithrombotic activity is relatively enhanced, and an application range is widened.

The collected precipitates formed by adding ethanol to the fruit juice or extract used as it is, or a concentrate of the fruit juice or the extract, after the removal of insoluble substances have further enhanced antithrombotic activity, and are preferable. The concentration of ethanol is not particularly limited. The ethanol concentration is preferably from 60 to 95% (v/v), more preferably from 70 to 90% (v/v), from the viewpoint of yield and improvement in activity. The term "precipitates" as used herein refers to a substance which is precipitated when a solution containing precipitates is centrifuged, for instance, at 25° C. at 2000 rpm or higher.

The extract may be used as it is, or the extract may be used by drying the solution into a powder by means such as spray-drying or lyophilization, as desired.

The content of the fruit of amla in the antithrombotic composition of the present invention is preferably from 10 to 100% by weight on a dry basis. Taking into consideration convenience of use of the composition, the content is more preferably from 20 to 90% by weight on a dry basis. The content of the fruit juice of amla is preferably from 5 to 100% by weight on a dry basis. Taking into consideration convenience of use of the composition, the content is more preferably from 10 to 95% by weight on a dry basis. The content of an extract thereof is preferably from 1 to 100% by weight on a dry basis. Taking into consideration convenience of use of the composition, the content is more preferably from 5 to 95% by weight based on a dry basis.

As the antithrombotic composition of the present invention, preferable are an antithrombotic composition in which the extract of fruit or fruit juice of amla is obtained by extracting fruit or fruit juice of amla with at least one member selected from the group consisting of water, bases and acids, and an antithrombotic composition containing precipitates obtained by fractionating with ethanol from an extract of fruit or fruit juice of amla, or fruit juice of amla.

It is preferable that the extract in the fibrin formation inhibitory composition of the present invention is prepared as follows. Matters other than those described below are the same as those for the above-mentioned antithrombotic composition.

As the extraction solvent, water, a base, an acid, or other hydrophilic solvent can be used. The hydrophilic solvent is preferably a lower alcohol such as methyl alcohol, ethyl alcohol, n-propyl alcohol, isopropyl alcohol or butyl alcohol, and acetone, from the viewpoint of operability and extraction efficiency. Especially preferable is at least one member selected from the group consisting of water, bases and acids.

The fruit juice or extraction may be used as it is. It is preferable to remove insoluble substances by filtration or centrifugation, because the fibrin formation inhibitory activity is relatively enhanced, and an application range is widened.

The collected precipitates formed by adding ethanol to the fruit juice or extract as it is, or a concentrate of the fruit juice or the extract, after removal of insoluble substances have further higher fibrin formation inhibitory activity, and are preferable. The concentration of ethanol is not particularly limited, and the concentration is preferably from 20 to 80% (v/v), and more preferably from 60 to 80% (v/v) from the viewpoint of enhancement in action.

Further, those prepared by purifying precipitates obtained by addition of ethanol using chromatography or column are preferable because they can be obtained as a fraction having further higher fibrin formation inhibitory action. The chromatography and column are not particularly limited, and for instance, ion exchange chromatography, gel filtration chromatography, hydrophobic chromatography, adsorption column chromatography, affinity chromatography, reverse phase column chromatography, ion exchange column, gel filtration column, hydrophobic column, or reverse phase column can be used. The gel filtration chromatography or gel filtration column is desirable from the viewpoint of purification efficiency.

The content of the fruit of amla in the fibrin formation inhibitory composition of the present invention is preferably from 10 to 100% by weight on a dry basis. Taking into consideration convenience of use of the composition, the content is more preferably from 20 to 90% by weight on a dry basis. The content of the fruit juice of amla is preferably from 5 to 100% by weight on a dry basis. Taking into consideration convenience of use of the composition, the content is more preferably from 10 to 95% by weight on a dry basis. The content of an extract thereof is preferably from 1 to 100% by weight on a dry basis. Taking into consideration convenience of use of the composition, the content is more preferably from 5 to 95% by weight on a dry basis.

As the fibrin formation inhibitory composition of the present invention, preferable are a fibrin formation inhibitory composition in which an extract of fruit or fruit juice of amla is obtained by extracting the fruit or fruit juice of amla with at least one member selected from the group consisting of water, bases, acids and hydrophilic solvents, and a fibrin formation inhibitory composition containing precipitates fractionated with ethanol from an extract of the fruit or fruit juice of amla, or the fruit juice of amla.

It is preferable that an extract in the anti-platelet aggregation composition of the present invention is prepared as follows. Matters other than those described below are the same as those for the above-mentioned antithrombotic composition.

The fruit juice or the extract may be used as it is. It is preferable to remove insoluble substances by filtration or centrifugation, because the anti-platelet action is relatively enhanced and an application range is widened.

The collected supernatant (containing soluble fraction) obtained by adding ethanol to the fruit juice or extract as it is, or a concentrate of the fruit juice or the extract, after removal of insoluble substances has further enhanced anti-platelet action, and is preferable. The concentration of ethanol is not particularly limited, and preferably from 10 to 90% (v/v), more preferably from 10 to 30% (v/v), from the viewpoint of enhancement in action. The supernatant as used herein refers to a residual solution obtained by removing substances precipitated upon centrifugation of a liquid containing a precipitate, for instance, at 25° C. at 2000 rpm or higher.

The content of the fruit of amla in the anti-platelet aggregation composition of the present invention is preferably from 10 to 100% by weight on a dry basis. Taking into consideration convenience of use of the composition, the content is more preferably from 20 to 90% by weight on a dry basis. The content of the fruit juice of amla is preferably from 5 to 100% by weight on a dry basis. Taking into consideration convenience of use of the composition, the content is more preferably 10 to 95% by weight on a dry basis. The content of an extract thereof is preferably from 1 to 100% by weight on a dry basis. Taking into consideration convenience of use of the composition, the content is more preferably from 5 to 95% by weight on a dry basis.

As the anti-platelet aggregation composition of the present invention, preferable are an anti-platelet aggregation composition in which an extract of fruit or fruit juice of amla is obtained by extracting fruit or fruit juice of amla with at least one member selected from the group consisting of water, bases and acids, and an anti-platelet aggregation composition containing a soluble fraction fractionated with ethanol from the extract of the fruit or fruit juice of amla or the fruit juice of amla.

It is preferable that an extract in the platelet aggregation inhibitory composition of the present invention is prepared as follows. Matters other than those described below are the same as those for the above-mentioned antithrombotic composition.

As the extraction solvent, a hydrophilic solvent or acetone can be used besides water, the base or the acid. The hydrophilic solvent is preferably one or more kinds selected from the group consisting of lower alcohols such as methyl alcohol, ethyl alcohol, n-propyl alcohol, isopropyl alcohol and butyl alcohol from the viewpoint of operability and extraction efficiency. Especially preferable is at least one member selected from the group consisting of water, bases and acids.

The fruit juice or the extract may be used as it is. It is preferable to remove insoluble substances and the solvents by filtration, centrifugation or fractional distillation, because the anti-platelet action is relatively enhanced so that its application range is widened.

After removal of insoluble substances and a solvent, the fruit juice or extract as it is, or a concentrate thereof is distributed with an organic solvent, and each of solvent-soluble fractions may be obtained. These solvent-soluble fractions are preferable because of their further enhanced anti-platelet action. As the organic solvent, a lower alcohol such as methyl alcohol, ethyl alcohol, n-propyl alcohol, isopropyl alcohol or butyl alcohol, ethyl acetate, butyl acetate, diethyl ether, methyl ether, methyl isobutyl ketone, hexane, acetone or chloroform can be used. In order to increase purity of the soluble fraction, the distribution with other hydrophobic solvent may be combined. It is preferable to use ethyl alcohol. The concentration of these solvents is not particularly limited. The final concentration is preferably from 20 to 80% (v/v), more preferably from 20 to 60% (v/v), from the viewpoint of yield and enhancement in action.

Purification may be carried out by chromatography or column using a phenolic, styrenic, acrylic acid-based, epoxy amine-based, pyridine-based or methacrylic hydrophobic resin as a matrix, for the purpose of further enhancing purity. In this case, as an eluent after resin adsorption, a lower alcohol such as methyl alcohol, ethyl alcohol, n-propyl alcohol, isopropyl alcohol or butyl alcohol, and acetone can be used alone, or in the form of an aqueous solution.

The content of fruit of amla in the platelet aggregation inhibitory composition of the present invention is preferably from 10 to 100% by weight on a dry basis. Taking into consideration convenience of use of the composition, the content is more preferably from 20 to 90% by weight on a dry basis. The content of fruit juice of amla is preferably from 5 to 100% by weight on a dry basis. Taking into consideration convenience of use of the composition, the content is more preferably from 10 to 95% by weight on a dry basis. The content of an extract thereof is preferably from 1 to 100% by weight on a dry basis. Taking into consideration convenience of use of the composition, the content is more preferably from 5 to 95% by weight on a dry basis.

As the platelet aggregation inhibitory composition of the present invention, preferable are a platelet aggregation inhibitory composition in which an extract of fruit or fruit juice of amla is obtained by extracting fruit or fruit juice of amla with at least one member selected from the group consisting of water, bases, acids, hydrophilic solvents and acetone, and a platelet aggregation inhibitory composition containing a fraction obtained by fractionating an extract of fruit or fruit juice of amla with an organic solvent, preferably at least one kind selected from the group consisting of methyl alcohol, ethyl alcohol, n-propyl alcohol, isopropyl alcohol, butyl alcohol, ethyl acetate, butyl acetate, diethyl ether, methyl ether, methyl isobutyl ketone, hexane or chloroform.

In addition, in the extraction procedure of an extract used in each composition of the present invention mentioned above, it is preferable to carry out an enzymatic treatment before the extraction and/or during the extraction of extraction raw materials, because the yield and flavor can be improved, and a composition having high action can be obtained by carrying out together an enzymatic treatment. The pH during the enzymatic treatment can be properly selected using, as an index, an optimal pH and pH stability of the enzyme to be used. In addition, the temperature during the treatment can be properly selected using, as an index, an optimal temperature and temperature stability of the enzyme to be used. An enzyme used in the enzymatic treatment of the present invention is not particularly limited as long as the enzyme is used in food industries. There may be used one kind selected from pectinase, cellulase, hemicellulase, α-amylase, glucoamylase, maltotriohydrolase, β-amylase, transglucosidase, lipase, protease, glutaminase, nuclease, deaminase, dextranase, glucose oxidase, lactase, tannase, chlorogenic acid esterase, pullulanase, trypsin, papaine, rennet, phospholipase $A_2$ and the like, or in admixture of two or more kinds. Preferably, there may be used one kind selected from pectinase, cellulase, hemicellulase, protease, chlorogenic acid esterase and tannase, or in admixture of two or more kinds. The amount of the enzyme to be used is not particularly limited. Although the amount of the enzyme is different depending upon the kinds of enzymes, the amount is preferably from 0.05 to 2 parts by weight based on 100 parts by weight of a dried extraction raw material. The enzymatic treatment may be carried out in the same manner for the fruit or fruit juice of amla.

Therefore, as the composition of the present invention as mentioned above, a composition comprising fruit, fruit juice or an extract thereof of amla which has been subjected to an enzymatic treatment is more preferable.

Anti-thrombosis (or antithrombotic) in the antithrombotic composition of the present invention is not particularly limited, and preferably refers to an action of inhibiting formation of thrombus (anti-coagulant action). The antithrombotic effect can be confirmed by measuring an activated partial thromboplastin time (APTT), which is a method of measuring anti-coagulant activity on an intrinsic blood coagulation system as shown, for instance, in Test Example A-1 set forth below.

The fibrin formation inhibitory effect in the fibrin formation inhibitory composition of the present invention can be confirmed by adding 300 microliters of a fibrin formation inhibitory composition to 3 milliliters of a 0.7% fibrinogen test solution, mixing the mixture thoroughly, adding 300 microliters of a thrombin test solution (10 U/ml) thereto to form and coagulate fibrin, measuring its coagulation weight, and examining an fibrin formation inhibitory ratio as shown, for instance, in Test Example A'-1 set forth below. Usually, the fibrin formation inhibitory ratio is preferably 20% or more, more preferably 30% or more.

The anti-platelet aggregation in the anti-platelet aggregation composition of the present invention refers to inhibition of the aggregation of platelets, and is also simply referred to as anti-platelet. The anti-platelet activity can be confirmed by a method of determining a platelet aggregation ratio using an aggregometer when an aggregation-causing substance (ADP, epinephrine, collagen, arachidonic acid or the like) is added to platelet rich plasma or collected blood as shown, for instance, in Test Example A"-1 set forth below.

The platelet aggregation inhibition in the platelet aggregation inhibitory composition of the present invention refers to inhibition of the aggregation of platelets, and is also simply referred to as anti-platelet. The anti-platelet activity can be confirmed by a method of determining a platelet aggregation ratio using a whole blood platelet aggregation analyzer (Aggregometer) when ristocetin, an agonist for causing platelet aggregation due to cross-linking formation between collagen and GpIg by vWF was added to the collected blood as shown, for instance, in Test Example A'''-1 set forth below.

The composition of the present invention can be applied to foodstuff, medicaments, feeds and the like, and foodstuff or medicaments which can be easily contacted by human are preferable. The details of those application examples will be described later.

The amount of the composition of the present invention to be taken as foodstuff may be appropriately adjusted depending upon individual cases by taking into consideration physical conditions, weight, age or sex of an individual to be administered, and the like. The number of times taken, the time period, timing and the like are not limited, and the composition may be taken, for instance, once a day or in divided portions of a several times a day.

The amount of the composition of the present invention to be taken as the foodstuff is usually from 0.05 to 20 g/day, preferably from 0.1 to 5 g/day per 50 kg weight of one human individual as the composition.

The dose of the composition of the present invention as a medicament may be properly determined depending upon individual cases taking into consideration an administration method, symptoms of a disease, and weight, age or sex of an individual to be administered, and the like. The number of times of administration, a time period, timing and the like are not limited, and for instance, the composition can be administered once a day or in divided portions of several times a day.

The dose of the composition of the present invention as a medicament is usually from about 40 mg to about 3 g/day, preferably from 100 to 500 mg/day per 50 kg weight of an adult in terms of the amount of the active ingredient on a dry weight.

(2) Tea

Specifically, the present invention provides a composition for anti-thrombus and a composition for anti-platelet aggregation, characterized in that each composition comprises an extract of tea as an active ingredient.

The composition of the present invention exhibits its effect based on the action owned by the above-mentioned tea component. The following action for the tea component has been found for the first time in the present invention.

In other words, for the above-mentioned tea component, it was seen from the result of measurement of an activated partial thromboplastin time (APTT) that the effect of inactivating a factor involved in an intrinsic pathway to inhibit fibrin formation and inhibit formation of thrombus in a blood vessel is enhanced.

It was seen from the results of the platelet aggregation test for the above-mentioned tea component that the effect of inhibiting formation of a platelet aggregate is enhanced. In other words, for the above-mentioned tea component, it was seen from the results of the test of platelet aggregation caused when ADP which is an agonist for inducing a binding step with other platelet via fibrinogen by GpIIb-IIIa to cause platelet aggregation is added, a so-called ADP-induced platelet aggregation, that the effect of inhibiting the platelet aggregation by inhibiting a binding step with other platelet via fibrinogen by GpIIb-IIIa is enhanced.

The tea used in the present invention is not particularly limited. Botanically, the tea includes green tea which is an unfermented tea, oolong tea which is a hemifermented tea, and a black tea which is a fermented tea, each being prepared from a leaf of a plant belonging to the Theaceae family. Among them, the use of the green tea which is an unfermented tea is used more preferably from the viewpoint of its effect.

It is preferable in the tea extract of the present invention that a polyphenol which is a bitterness component is reduced from the viewpoint of flavor.

As the method of removing a polyphenol, which is a bitterness component, there have been generally known a method of adding polyvinyl polypyrrolidone to an extract (Japanese Patent Laid-Open No. Hei 1-218550) and a method of removing a polyphenol together with water to be dehydrated by frozen concentration (Japanese Patent Laid-Open No. 2002-325539), and can be utilized.

The method of determining a polyphenol content in the present invention is not particularly limited. Examples include an iron tartrate colorimetry and a Folin-Ciocalteu method, and the iron tartrate colorimetry is desirable. The polyphenol content is preferably 15% by weight or less, more preferably 10% by weight or less in the solid content of the tea extract from the viewpoint of taste.

Here, for instance, when the purpose is to collect the polyphenol, the residue after the extraction of the polyphenol from water or hot water extract of tea indeed corresponds to the "tea extract with reduced polyphenol" of the present invention. Since the polyphenol has the nature of being easily dissolved in a specified organic solvent when fractionation, for instance, is carried out with the specified organic solvent, a majority of the polyphenol is dissolved in an organic solvent side (water-insoluble fraction), and is hardly contained in an aqueous fraction. In other words, the "tea extract with reduced polyphenol" is obtained from a water migration fraction when tea leaves or powder tea leaves are extracted with water or hot water, and the extract is distributed in a solvent such as ethyl acetate or acetone. In addition, recent years, in view of various functionalities owned by the polyphenol, the utilization of the polyphenol has been increased. The component after the extraction of the polyphenol from a hot water extract of tea is handled as a by-product (or residue), and is mostly discarded without being utilized effectively. Regarding this matter, according to the present invention, since the component which has not been so far discarded without being effectively utilized is effectively utilized, all of a hot water extract of tea can be utilized, leading to some advantages of improvement in economic advantages, and reduction in a discarded amount of wastes.

In addition, it is preferable in the tea extract of the present invention that caffeine which serves to increase the concentrations of prothrombin and fibrinogen in blood that cause blood coagulation is reduced.

As the method of removing caffeine, a method of using an acidic clay (Japanese Patent Laid-Open No. Hei 06-142405), a method of using an active carbon (Japanese Patent Laid-Open No. Hei 08-070772), a method of using a synthetic adsorbent (Japanese Patent Laid-Open No. Hei 08-109178) and the like have been generally known, and can be utilized.

The method of measuring caffeine is not particularly limited. The method includes, for instance, high-performance liquid chromatography. The caffeine content is preferably 2% by weight or less, more preferably 1% by weight or less in the solid content of the tea extract.

The above-mentioned method for separating a tea extract from an aqueous fraction obtained by distribution of the water or hot water extract of tea in ethyl acetate or acetone is preferable because caffeine can be reduced together with the polyphenol.

The method for extracting tea is not particularly limited. For instance, when water or hot water is used as an extraction solvent, the extraction solvent may be preferably used in an amount of from 500 to 5000 parts by weight, based on 100 parts by weight of the dry extraction raw material. The extraction temperature is preferably from 40° to 100° C. The extraction may be carried out while allowing the mixture to stand, or while stirring.

Further, in the above-mentioned extraction, it is preferable to repeat the step of extracting the extraction residue again one or more times, because the extraction ratio is improved. The solvent used in extraction in this case may be the same, or different solvents may be used.

The above-mentioned extract may be used as it is. It is preferable to remove insoluble substances by filtration or centrifugation, so that the anti-thrombotic effect or the anti-platelet aggregation effect is enhanced, and an application range is widened.

The collected precipitates obtained by adding ethanol to an extract after the removal of insoluble substances have a further enhanced anti-thrombotic effect or anti-platelet aggregation effect, and are preferable. The concentration of ethanol is not particularly limited. The final concentration is preferably from 10 to 50% (v/v), more preferably from 15 to 45% (v/v) from the viewpoint of yield and improvement in action.

The extract may be used as it is, or can be used by drying, as desired.

The content of the tea extract in the composition for anti-thrombus or the composition for anti-platelet aggregation of the present invention is preferably from 5 to 100% by weight on a dry basis. Taking into consideration convenience of use of the composition, the content is more preferably from 10 to 90% by weight on a dry basis.

As the composition for anti-thrombus or the composition for anti-platelet aggregation of the present invention, preferable are a composition in which a tea extract is a tea extract with reduced polyphenol, a composition in which a tea extract is a tea extract with reduced caffeine, and a composition in which a tea extract is precipitates obtained by further fractionating with ethanol a tea extract with reduced polyphenol and/or caffeine.

Anti-thrombus in the composition for anti-thrombus of the present invention is not particularly limited, and preferably is an action of inhibiting formation of thrombus (anti-coagulant action). The measurement of the anti-thrombotic effect is not particularly limited. The anti-thrombotic effect can be confirmed by measuring an activated partial thromboplastin time (APTT) in the method of assaying the anti-coagulant activity on an intrinsic blood coagulation system as shown, for instance, in Test Example B-1 set forth below.

The anti-platelet aggregation in the composition for anti-platelet aggregation of the present invention refers to inhibition of platelet aggregation, and is also simply referred to as anti-platelet. The anti-platelet activity can be confirmed by the method of determining a platelet aggregation ratio using an aggregometer when an aggregation-causing substance (ADP, epinephrine, collagen, arachidonic acid and the like) is added to platelet rich plasma or collected blood as shown, for instance, in Test Example B'-1 set forth below.

The composition of the present invention can be applied to foodstuff, medicaments, feeds and the like, preferably, foodstuff or medicaments which can be easily contacted by human. The details of application examples thereof will be described later.

The amount of intake of the composition of the present invention as foodstuff may be properly adjusted depending upon individual cases by taking into consideration physical conditions, weight, age or sex of an individual to be administered, and the like. The number of times of intake, time periods, timing and the like are not particularly limited. For instance, the composition can be taken once a day or in divided portions of several times a day.

The amount of intake of the composition of the present invention as foodstuff is usually from 0.05 to 20 g/day, preferably from 0.1 to 5 g/day per 50 kg weight of one human individual as the composition.

The dose of the composition of the present invention as a medicament may be properly determined depending upon individual cases taking into consideration an administration method, symptoms of a disease, and weight, age or sex of an individual to be administered, and the like. The number of times of administration, time periods, timing and the like are not limited. For instance, the medicament can be administered once a day or in divided portions of several times a day.

The dose of the composition of the present invention as the medicament is usually from about 50 mg to about 3 g/day, preferably from 100 to 500 mg/day per 50 kg weight of one adult individual in terms of the amount of the active ingredient on a dry basis.

(3) *Hibiscus*

Specifically, the present invention provides an anti-blood coagulant composition, a platelet aggregation preventing composition, and a composition for preventing platelet aggregation, characterized in that each composition comprises, as an active ingredient, at least one member selected from the group consisting of fruit, fruit juice and leaf of *hibiscus* and an extract thereof.

The composition of the present invention exhibits its effect based on an action owned by the above-mentioned *hibiscus* component. The following action for the *hibiscus* component has been found for the first time in the present invention.

In other words, it was seen from the results of the measurement of an activated partial thromboplastin time (APTT) for the above-mentioned *hibiscus* component, that the effect of inactivating a factor involved in an intrinsic pathway to inhibit fibrin formation and inhibit thrombus formation in a blood vessel is enhanced.

For the above-mentioned *hibiscus* component, it was seen from the results of a test for platelet aggregation caused when ADP, which is an agonist for causing the platelet aggregation by inducing a binding step with other platelet by GpIIb-IIIa via fibrinogen is added, a so-called ADP-induced platelet aggregation, that the effect of inhibiting platelet aggregation thrombus formation is enhanced by inhibiting a binding step with other platelet by GpIIb-IIIa via fibrinogen.

For the above-mentioned *hibiscus* component, it was seen from the results of the test for platelet aggregation caused when ristocetin, which is an agonist for causing the platelet aggregation by cross-linking formation between collagen and GpIb by vWF, is added, a so-called ristocetin-induced platelet aggregation, that the anti-platelet aggregation effect is enhanced by inhibiting cross-linking formation between collagen and GpIb by vWF.

*Hibiscus* used in the present invention has a scientific name of *Hibiscus*, and is called *Buttsusoge* in Japanese. *Hibiscus* is an evergreen shrub belonging to Malvaceae *Hibiscus* and, as an etymology, *hibiscus* is derived from goddess of beauty Hibis of ancient Egypt. The place of origin is Southern China, Eastern India, South Pacific archipelago and Tropical Africa. *Hibiscus* has fresh sour taste, and is recently used as a source in French cuisine or Italian cuisine. Edible *hibiscus* species used as a herb has a scientific name of *Hibiscus sabdariffa*, is called roselle (United Kingdom) or Florida cranberry (U.S.A.), and is cultivated in countries such as Jamaica, Sudan, Egypt, Thailand, China, Suriname and Malaysia.

In the present invention, as a part of *Hibiscus*, fruit, fruit juice, leaf or an extract thereof is used, and preferably, fruit petal derived from calyx and flower, or leaf portion is used. Its form is not particularly limited, and any of raw fruit, dry fruit, fruit powder, raw leaf, dry leaf, dry leaf powder and the like may be used.

In the case of the fruit juice or fruit juice powder, the fruit juice or fruit juice powder may be used as it is. It is preferable to remove water-insoluble components by extraction because raw fruit, dry fruit, raw leaf, dry leaf or the like contains water-insoluble components.

When raw fruit, dry fruit, raw leaf or dry leaf is used as the extraction raw material during the extraction, it is preferable to use one obtained by crushing and mixing the extraction raw material thoroughly with a mixer or the like in order to increase extraction efficiency.

When the dry fruit or dry leaf is used, it is preferable that a raw material is pulverized to a particle size of 40 mesh or smaller in order to increase extraction efficiency.

The extraction method is not particularly limited in an extraction solvent, an extraction temperature and the like. As the extraction solvent, water, a base, an acid, a hydrophilic solvent or acetone can be used. As the hydrophilic solvent, one or more kinds selected from the group consisting of lower alcohols such as methyl alcohol, ethyl alcohol, n-propyl alcohol, isopropyl alcohol and butyl alcohol are preferable from the viewpoint of operability and extraction efficiency. Especially preferable is at least one member selected from the group consisting of water, bases and acids.

When the acid or base is used as the extraction solvent, it is preferable to neutralize an extract. A salt produced by a neutralization reaction can be removed by a known method such as a dialysis method or gel filtration. When water is used as the extraction solvent, since the neutralization reaction as mentioned above is not necessary, and removal of the formed salt is not necessitated, it is further preferable to use water.

The acid used during the extraction is not particularly limited, and most of acids can be used. It is preferable to use one kind selected from hydrochloric acid and sulfuric acid, or a combined use thereof, from the viewpoint of easy availability and handling property.

In addition, the base is not particularly limited, and most of bases can be used. It is preferable to use one kind selected from sodium hydroxide and potassium hydroxide, or a combined use thereof.

The concentration of the acid or base used in the extraction is not particularly limited regardless of the extract before or after the enzymatic treatment. The concentration of the acid or base varies depending upon the strength of the acid or base. It is preferable that the acid or base is used in a concentration of from 0.01 to 0.5 molar, from the viewpoint of operability and extraction efficiency. Usually, the acid or base is used as an aqueous solution having the concentration.

The extraction solvent may be preferably used in an amount of from 500 to 5000 parts by weight based on 100 parts by weight of the dry extraction raw material. The extraction temperature is preferably from 40° to 70° C. The extraction may be carried out while allowing the mixture to stand, or while stirring.

Further, in the above-mentioned extraction, it is preferable to repeat the step of extracting against the extraction residue once or more times, because the extraction efficiency is improved, and the yield is improved. The solvent used in the extraction in this case may be the same, or different solvents may be used.

The above-mentioned extract can be used as it is. It is preferable to remove insoluble substances and solvents by filtration, centrifugation and fractional distillation, because the anti-blood coagulant effect or anti-platelet aggregation effect is enhanced, so that its application range is widened.

Incidentally, in the extraction procedure of the extract used in each of the above-mentioned compositions of the present invention, it is preferable to carry out the enzymatic treatment before the extraction and/or during the extraction of the extraction raw material, because the yield and the flavor can be improved and the composition having a high action is obtained by carrying out the enzymatic treatment together therewith. The pH during the enzymatic treatment can be properly selected using an optimal pH and a pH stability of the enzyme used as an index. In addition, the temperature during the treatment can be properly selected using an optimal temperature and a temperature stability of the enzyme used as an index. The enzyme used in the enzymatic treatment in the present invention is not limited, as long as the enzyme is those which are used in food industries, without being not particularly limited thereto. The enzyme includes one kind selected from pectinase, cellulase, hemicellulase, Q-amylase, glucoamylase, maltotriohydrolase, β-amylase, transglucosidase, lipase, protease, glutaminase, nuclease, deaminase, dextranase, glucose oxidase, lactase, tannase, chlorogenic acid esterase, pullulanase, trypsin, papain, rennet, phospholipase $A_2$ and the like or two or more kinds of them. Preferably, one kind selected from pectinase, cellulase, hemicellulase, protease, chlorogenic acid esterase, and tannase can be used, or two or more kinds of them may be used in combination. The amount of the enzyme used is not particularly limited. The amount may differ depending upon the kinds of enzymes, and it is preferable that the enzyme is used in an amount of from 0.05 to 2 parts by weight based on 100 parts by weight of the dry extraction raw material. The enzymatic treatment may be carried out in the same manner on the fruit, fruit juice or leaf of *hibiscus*.

Therefore, as the composition of the present invention as mentioned above, a composition comprising fruit, fruit juice or leaf of *hibiscus*, or an extract thereof which has been subjected to enzymatic treatment is more preferable.

On the other hand, after removal of insoluble substances and solvents described above, the fruit juice or extract as it is, or a concentrate of the fruit juice or extract is distributed with an organic solvent, and each solvent-soluble fraction may be obtained. These solvent-soluble fractions have further enhanced anti-blood coagulant effect or anti-platelet aggregation effect, and are preferable. As the organic solvent, a lower alcohol such as methyl alcohol, ethyl alcohol, n-propyl alcohol, isopropyl alcohol and butyl alcohol, ethyl acetate, butyl acetate, diethyl ether, methyl ether, methyl isobutyl ketone, hexane, acetone or chloroform can be used. The distribution with other hydrophobic solvent may be combined in order to enhance purity of the soluble fraction, and ethyl alcohol is preferable. The concentration of these solvents is not particularly limited, and a final concentration is preferably from 20 to 80% (v/v), more preferably from 20 to 60% (v/v), from the viewpoint of yield and effects.

For the purpose of further enhancing the purity, the purification may be carried out by chromatography or column using a phenolic, styrenic, acrylic acid-based, epoxy amine-based, pyridine-based or methacrylic hydrophobic resin as a matrix. In this case, as an eluent after resin adsorption, a lower alcohol such as methyl alcohol, ethyl alcohol, n-propyl alcohol, isopropyl alcohol or butyl alcohol, and acetone can be used alone, or in the form of an aqueous solution.

The extract and the fraction may be used as they are. Alternatively, the extract and the fraction may be used by drying into a powder by means such as spray-drying or lyophilization, as desired.

The content of the fruit of *hibiscus* in the anti-blood coagulant composition of the present invention is preferably from 10 to 100% by weight on a dry basis. Taking into consideration convenience of use of the composition, the content is more preferably from 20 to 90% by weight on a dry basis. The content of the fruit juice of *hibiscus* is preferably from 5 to 100% by weight on a dry basis. Taking into consideration convenience of use of the composition, the content is more preferably from 10 to 95% by weight on a dry basis. The content of the leaf of *hibiscus* is preferably from 10 to 100% by weight on a dry basis. Taking into consideration convenience of use of the composition, the content is more preferably from 20 to 90% by weight on a dry basis. The content of the extract thereof is preferably from 1 to 100% by weight on a dry basis. Taking into consideration convenience of use of the composition, the content is more preferably from 5 to 95% by weight on a dry basis.

The content of the fruit of *hibiscus* in the platelet aggregation preventing composition or the composition for preventing platelet aggregation of the present invention is preferably from 10 to 100% by weight on a dry basis. Taking into consideration convenience of use of the composition, the content is more preferably from 20 to 90% by weight on a dry basis. The content of the fruit juice of *hibiscus* is preferably from 5 to 100% by weight on a dry basis. Taking into consideration convenience of use of the composition, the content is more preferably from 10 to 95% by weight on a dry basis. The content of the leaf of *hibiscus* is preferably from 10 to 100% by weight on a dry basis. Taking into consideration convenience of use of the composition, the content is more preferably from 20 to 90% by weight on a dry basis. The content of the extract thereof is preferably from 1 to 100% by weight on a dry basis. Taking into consideration convenience of use of the composition, the content is more preferably from 5 to 95% by weight on a dry basis.

As the anti-blood coagulant composition, the platelet aggregation preventing composition or the composition for preventing platelet aggregation of the present invention, preferable are a composition in which an extract of fruit, fruit juice or leaf of *hibiscus* is obtained by extracting fruit, fruit juice or leaf of *hibiscus* with at least one kind selected from the group consisting of water, bases, acids, hydrophilic solvents and acetone, and a composition containing a fraction obtained by fractionation of an extract of fruit, fruit juice or leaf of *hibiscus* with an organic solvent, preferably with at least one kind selected from the group consisting of methyl alcohol, ethyl alcohol, n-propyl alcohol, isopropyl alcohol, butyl alcohol, ethyl acetate, butyl acetate, diethyl ether, methyl ether, methyl isobutyl ketone, hexane and chloroform.

The anti-blood coagulant effect in the anti-blood coagulant composition of the present invention can be confirmed by measuring an activated partial thromboplastin time (APTT), which is a method of assaying anti-blood coagulant activity on an intrinsic blood coagulation system as shown, for instance, in Test Example C-2 set forth below.

The platelet aggregation in the platelet aggregation preventing composition of the present invention refers to inhibition of platelet aggregation, and is also simply referred to as anti-platelet. The anti-platelet activity can be confirmed according to the method of measuring a platelet aggregation ratio using a whole platelet aggregation analyzer (Aggregometer) when ADP, which is an agonist for causing platelet aggregation by inducing a binding step with other platelet by GpIIb-IIIa via fibrinogen, is added to collected blood as shown, for instance, in Test Example C'-1 set forth below.

The anti-platelet aggregation in the composition for preventing platelet aggregation of the present invention refers to inhibition of platelet aggregation, and is also referred to as anti-platelet. The anti-platelet activity can be confirmed according to the method of determining a platelet aggregation ratio using a whole platelet aggregation analyzer (Aggregometer) when ristocetin, which is an agonist for causing platelet aggregation by cross-linking formation between collagen and GpIb by vWF, is added to collected blood as shown, for instance, in Test Example C"-1 set forth below.

The composition of the present invention can be applied to foodstuff, medicaments, feeds and the like, preferably foodstuff or medicaments which can be easily contacted by human. The details of application examples thereof will be described later.

The amount of intake of the composition of the present invention as foodstuff may be properly adjusted depending upon individual cases by taking into consideration physical conditions, weight, age, sex and the like of an individual to be administered. The number of times of intake, time periods, timing and the like are not particularly limited. For instance, the foodstuff can be taken once a day or in divided portions of several times a day.

The amount of intake of the composition of the present invention as foodstuff is usually from 0.05 to 20 g/day, preferably from 0.1 to 5 g/day per 50 kg weight of one human individual as the composition.

The dose of the composition of the present invention as the medicament may be appropriately determined depending upon individual cases taking into consideration an administration method, symptoms of diseases, and weight, age, sex or the like of an individual to be administered, and the like. The number of times of administration, time periods, timing and the like are not limited. For instance, the composition can be administered once a day or in divided portions of several times a day.

The dose of the anti-blood coagulant composition of the present invention as the medicament is usually from about 50 mg to about 2 g/day, preferably from 100 to 500 mg/day per 50 kg weight of one adult individual in terms of the amount of the active ingredient on a dry basis.

The dose of the platelet aggregation preventing composition or the composition for preventing platelet aggregation of the present invention as the medicament is usually from about 40 mg to about 3 g/day, preferably from 100 to 500 mg/day per 50 kg weight of one adult individual in terms of the amount of the active ingredient on a dry basis.

(4) Cocklebur

Specifically, the present invention provides a platelet aggregation thrombus inhibitory composition, and a composition for inhibiting platelet aggregation thrombus, characterized in that each composition comprises, as an active ingredient, at least one member selected from the group consisting of fruit, fruit juice and seed of cocklebur and an extract thereof.

The composition of the present invention exhibits its effect based on the action owned by the above-mentioned cocklebur component. The following action for the cocklebur component has been found for the first time in the present invention.

In other words, for the above-mentioned cocklebur component, it was seen from the results of the test for platelet aggregation caused when ADP, which is an agonist for causing platelet aggregation by inducing a binding step with other platelet by GpIIb-IIIa via fibrinogen, is added, a so-called ADP-induced platelet aggregation, that the effect of inhibiting platelet aggregation thrombus formation is enhanced by inhibiting a binding step with other platelet by GpIIb-IIIa via fibrinogen.

For the above-mentioned cocklebur component, it was seen from the results of the test of platelet aggregation caused when ristocetin, which is an agonist for causing platelet aggregation by cross-linking formation between collagen and GpIb by vWF is added, a so-called ristocetin-induced platelet aggregation, that effect of inhibiting platelet aggregation thrombus formation is enhanced by inhibiting cross-linking formation between collagen and GpIb by vWF.

Cocklebur used in the present invention has a scientific name of *Xanthium strumarium* L., is an annual herb belonging to *Compositae xanthium*, has a height of about 1 meter, and totally has a short bristle. Seeds are alternate on stem, the shape of the seed is approximately heart-shaped, a tip thereof is cuspidate, the seed edge is notched non-uniformly, and a seed is thick and slightly hard and has a short hair. In summer, a branched bough tip has a yellowish green capitate flower in a conical form. A male flower is at an upper part of the plant, and has green hard stab hairs. A female flower is at a lower part of the plant. Fruit is enveloped with an anther, has thorns at a periphery thereof, and is scattered by adhering to clothes or hairs of an animal. There are about 20 kinds of cockleburs in the world, and the place of origin is the Asian continent, and cockleburs are widely distributed in the world, many of which are distributed especially in the American continent. Since ancient Roman used cocklebur as a dye for staining hairs yellow, a genus name is *Xanthos* derived from yellow in Greek. In Japan, it is said that since when the seed is crumpled and is applied to skin, it is effective in bug-biting, it was named "Namomi (fresh crumpling)." In English, the plant is termed cocklebur. A crude drug prepared by drying a mature fruit of cocklebur with sunshine is referred to *Xanthium sibirucum*, which is used as antipyretic, a sweating agent or a headache drug. In Europe and North Africa, cocklebur is used as a feed for livestock, and is also used as a drug for treating swelling of lymph glands.

In the present invention, as a part of cocklebur, fruit, fruit juice, calyx, petal or seed is used. Its form is not particularly limited. In the case of the fruit, any of immature fruit, fully mature fruit, fruit juice powder and the like may be used.

In the case of the fruit juice or fruit juice powder, the fruit juice or fruit juice powder may be used as it is. When a substance containing a water-insoluble component such as a raw fruit or a dry fruit is used, it is preferable that the water-insoluble components have been removed by extraction from the viewpoint of enhancement in the effect.

When the raw fruit is used as the extraction raw material during the extraction, it is preferable to use a product obtained by crushing and mixing a raw material thoroughly with a mixer with or without addition of water after removing the seed, in order to enhance extraction efficiency.

When the dry fruit or dry seed is used as the extraction raw material, it is preferable that the raw material is pulverized to a particle size of 40 mesh or smaller, in order to enhance an extraction efficiency.

The extraction method is not particularly limited in an extraction solvent, an extraction temperature and the like. As the extraction solvent, water, bases, acids, hydrophilic solvents and acetone can be used. As the hydrophilic solvent, one or more kinds selected from the group consisting of lower alcohols such as methyl alcohol, ethyl alcohol, n-propyl alcohol, isopropyl alcohol and butyl alcohol are preferable from the viewpoint of operability and extraction efficiency. Especially preferable is at least one kind selected from the group consisting of water, bases and acids.

When the acid or base is used as the extraction solvent, it is preferable to neutralize an extract. A salt formed by a neutralization reaction can be removed by a known method such as a dialysis method or gel filtration. When water is used as the extraction solvent, since the above-mentioned neutralization reaction is not necessary, and removal of the formed salt is not necessitated, it is further preferable to use water.

The acid used during the extraction is not particularly limited, and most of acids can be used. It is preferable to use one kind selected from hydrochloric acid and sulfuric acid, or a combination of both, from the viewpoint of easy availability and operability.

The base is not particularly limited, and most of bases can be used. It is preferable to use one kind selected from sodium hydroxide and potassium hydroxide, and a combination of both.

The concentration of the acid or base used in the extraction is not particularly limited regardless of the extract before or after the enzymatic treatment. The concentration varies depending upon the strength of the acid or base. It is preferable that the acid or base is used in a concentration of from 0.01 to 0.5 molars, from the viewpoint of operability and extraction efficiency. Usually, the acid or base is used in the form an aqueous solution having the concentration.

The extraction solvent may be preferably used in an amount of from 500 to 5000 parts by weight based on 100 parts by weight of the dry extraction raw material. The extraction temperature is preferably from 40° to 70° C. The extraction may be carried out while allowing the mixture to stand, or while stirring.

Further, in the above-mentioned extraction, it is preferable to repeat again the step of extracting against an extract residue once or more times because the extraction efficiency is improved and the yield is improved. The solvent used in the extraction in this case may be the same, or different solvents may be used.

The extract can be used as it is. It is preferable to remove insoluble substances and solvents by filtration, centrifugation and fractional distillation, because the anti-platelet aggregation effect is enhanced, so that its application range is widened.

Incidentally, in the extraction procedure of the extract used in each of the above-mentioned compositions of the present invention, it is preferable to carry out the enzymatic treatment before the extraction and/or during the extraction of the extraction raw material because the yield and the flavor can be improved, and the composition having a high action is obtained by carrying out the enzymatic treatment together therewith. The pH during the enzymatic treatment can be properly selected using an optimal pH and a pH stability of the enzyme used as an index. In addition, the temperature during the treatment can be properly selected using an optimal temperature and a temperature stability of the enzyme used as an index. The enzyme used in the enzymatic treatment in the present invention is not limited, as long as the enzyme is those which are used in food industries, without being not particularly limited thereto. The enzyme includes one kind selected from pectinase, cellulase, hemicellulase, $\alpha$-amylase, glucoamylase, maltotriohydrolase, $\beta$-amylase, transglucosidase, lipase, protease, glutaminase, nuclease, deaminase, dextranase, glucose oxidase, lactase, tannase, chlorogenic acid esterase, pullanase, trypsin, papain, rennet, phospholipase $A_2$ and the like, or two or more kinds of them. Preferably, one kind selected from pectinase, cellulase, hemicellulase, protease, chlorogenic acid esterase and tannase may be used, or two or more kinds of them may be used in combination. The amount of the enzyme used is not particularly limited. The amount of the enzyme varies depending upon the kinds of enzymes. The amount is preferably from 0.05 to 2 parts by weight based on 100 parts by weight of the dry extraction raw material. In addition, the enzymatic treatment may be carried out in the same manner on fruit, fruit juice or seed of cocklebur.

Therefore, as the composition of the present invention as mentioned above, a composition comprising fruit, fruit juice or seed of cocklebur or an extract thereof which has been subjected to enzymatic treatment is more preferable.

On the other hand, the fruit juice or extract as it is, or a concentrate of the fruit juice or extract, after removal of insoluble substances and solvents as described above, may be distributed with an organic solvent, to give each solvent-soluble fraction. These solvent-soluble fractions have a further enhanced anti-platelet aggregation effect, and are preferable. As the organic solvent, there can be used a lower alcohol such as methyl alcohol, ethyl alcohol, n-propyl alcohol, isopropyl alcohol or butyl alcohol, ethyl acetate, butyl acetate, diethyl ether, methyl ether, methyl isobutyl ketone, hexane, acetone or chloroform. The distribution with other hydrophobic solvent may be combined in order to enhance purity of the soluble fraction, and ethyl alcohol is preferable. The concentration of these solvents is not particularly limited, and the final concentration is preferably from 20 to 80% (v/v), further preferably from 20 to 60% (v/v) from the viewpoint of yield and effects.

The purification may be carried out by chromatography or column using a phenolic, styrenic, acrylic acid-based, epoxy amine-based, pyridine-based or methacrylic hydrophobic resin as a matrix, for the purpose of further enhancing purity. In this case, as an eluent after resin adsorption, a lower alcohol such as methyl alcohol, ethyl alcohol, n-propyl alcohol, isopropyl alcohol or butyl alcohol, and acetone can be used alone, or in the form of an aqueous solution.

The extract and the fraction may be used as it is. Alternatively, the extract and the fraction may be used by drying into a powder by means such as spray-drying or lyophilization, as desired.

The content of the fruit of cocklebur in the platelet aggregation thrombus inhibitory composition or the composition for inhibiting platelet aggregation thrombus of the present invention is preferably from 10 to 100% by weight on a dry basis. Taking into consideration convenience of use of the composition, the content is more preferably from 20 to 90% by weight on a dry basis. The content of the fruit juice of cocklebur is preferably from 5 to 100% by weight on a dry basis. Taking into consideration convenience of use of the composition, the content is more preferably from 10 to 95% by weight on a dry basis. The content of the seed of cocklebur is preferably from 10 to 100% by weight on a dry basis. Taking into consideration convenience of use of the composition, the content is more preferably from 20 to 90% by weight on a dry basis. The content of the extract thereof is preferably from 1 to 100% by weight on a dry basis. Taking into consideration convenience of use of the composition, the content is more preferably from 5 to 95% by weight on a dry basis.

As the platelet aggregation thrombus inhibitory composition or the composition for inhibiting platelet aggregation thrombus of the present invention, preferable are a composition in which an extract of fruit, fruit juice or seed of cocklebur is obtained by extracting fruit, fruit juice or seed of cocklebur with at least one kind selected from the group consisting of water, bases, acids, hydrophilic solvents and acetone, and a composition containing a fraction obtained by fractionation of the extract of fruit, fruit juice or seed of cocklebur with an organic solvent, preferably at least one kind selected from the group consisting of methyl alcohol, ethyl alcohol, n-propyl alcohol, isopropyl alcohol, butyl alcohol, ethyl acetate, butyl acetate, diethyl ether, methyl ether, methyl isobutyl ketone, hexane and chloroform.

The platelet aggregation thrombus inhibition in the platelet aggregation thrombus inhibitory composition of the present invention refers to inhibition of thrombus formation by inhibiting the platelet aggregation, and the platelet aggregation is also simply referred to as anti-platelet. The anti-platelet activity can be confirmed by the method of determining a platelet aggregation ratio using a whole blood platelet aggregation analyzer (Aggregometer) when ADP, which is an agonist for causing platelet aggregation by causing a binding step with other platelet by GpIIb-IIIa via fibrinogen, is added to collected blood as shown, for instance, in Test Example D-1 set forth below.

The platelet aggregation thrombus inhibition in the composition for inhibiting platelet aggregation thrombus of the present invention refers to inhibition of thrombus formation by inhibiting the platelet aggregation, and the inhibition of the platelet aggregation is also simply referred to as anti-platelet. The anti-platelet activity can be confirmed by the method of determining a platelet aggregation ratio using a whole blood platelet aggregation analyzer (Aggregometer) when ristocetin, which is an agonist for causing platelet aggregation by the cross-linking formation between collagen and GpIb by vWT, is added to collected blood as shown, for instance, in Test Example D'-1 set forth below.

The composition of the present invention can be applied to foodstuff, medicaments, feeds and the like, preferably foodstuff or medicaments which can be easily contacted by human. The details of application examples thereof will be described later.

The amount of intake of the composition of the present invention as foodstuff may be properly adjusted depending upon individual cases taking into consideration physical conditions, weight, age or sex of an individual to be administered, and the like. The number of times of intake, time periods, timing and the like are not limited, and the foodstuff can be taken once a day or in divided portions of several times a day.

The amount of intake of the composition of the present invention as the foodstuff in the form of the composition is usually from 0.05 to 20 g/day, preferably from 0.1 to 5 g/day per 50 kg weight of one human individual.

The dose of the composition of the present invention as the medicament may be appropriately determined depending upon individual cases by taking into consideration an administration method, symptoms of diseases, and weight, age or sex of an individual to be administered, and the like. The number of times of administration, time periods, timing and the like are not limited, and for instance, the medicament can be administered once a day or in divided portions of several times a day.

The dose of the composition of the present invention as the medicament is usually from about 40 mg to about 3 g/day, preferably from 100 to 500 mg/day per 50 kg weight of one adult individual in terms of the amount of the active ingredient on a dry basis.

(5) *Gymnema*

Specifically, the present invention provides a thrombus formation inhibitory agent, characterized in that the composition comprises, as an active ingredient, *gymnema*, an extract thereof or a mixture thereof.

The composition of the present invention exhibits its effect based on the action owned by the above-mentioned *gymnema* component. The following action has been found for the *gymnema* component for the first time in the present invention.

In other words, it was seen from the results of the platelet aggregation test for the above-mentioned *gymnema* component that the effect of inhibiting formation of platelet aggregation is enhanced. In other words, for the above-mentioned *gymnema* component, it was seen from the results of a test for platelet aggregation caused when ADP, which is an agonist for causing platelet aggregation by inducing a binding step with other platelet by GpIIb-IIIa via fibrinogen is added, a so-called ADP-induced platelet aggregation, that the effect of inhibiting the platelet aggregation is enhanced by inhibiting a binding step with other platelet by GpIIb-IIIa via fibrinogen.

*Gymnema* used in the present invention has a scientific name of *Gymnema Sylvestre*, has the place of origin of India, and is an Asclepidaceae liana plant which is widely distributed in a tropical to subtropical district from Indonesia, Southwestern China and the like. From systematic botany, *gymnema* is a plant belonging to the same family as that of *Metaplexis japonica, Cynanchum caudatum, Asclepias curassavica* and the like which are also grown in Japan.

In the present invention, as a part of *gymnema*, usually, one or more kinds selected from the group consisting of leaf, stem and bine are used. Its form is not particularly limited. In the case of a powder, the powder may be used as it is. Alternatively, it is preferable to remove water-insoluble components by means of extraction with water or the like.

The extraction method is not particularly limited in the extraction solvent, the extraction temperature and the like. As the extraction solvent, water, a base, an acid, an alcohol, or a non-organic solvent such as an aqueous sodium chloride solution can be used. Preferable is one or more kinds selected from the group consisting of water, bases, acids and alcohols.

When the acid or base is used as the extraction solvent, it is preferable to neutralize an extract. A salt formed by the neutralization reaction can be removed by a known method such as a dialysis method or gel filtration. When water is used as the extraction solvent, since the neutralization reaction as mentioned above is not necessary, and removal of the formed salt is not necessitated, it is further preferable to use water.

The acid used during the extraction is not particularly limited, and most of acids can be used. Preferably, one kind selected from hydrochloric acid and sulfuric acid is used, or a combination of both may be used.

Also, the base is not particularly limited, and most of bases can be used. Preferably, one kind selected from sodium hydroxide and potassium hydroxide is used, or a combination of both may be used.

The concentration of the acid or base used in the extraction is not particularly limited. The concentration varies depending upon the strength of the acid or base. It is preferable that the acid or base is used in a concentration of from 0.01 to 0.5 molars. Usually, the acid or base is used in the form of an aqueous solution having such the concentration.

The alcohol in the present invention is not particularly limited. Preferable are those alcohols which can be used for preparing materials for foodstuff, and more preferable is one or more kinds selected from the group consisting of ethanol, isopropyl alcohol, propylene glycol and glycerol. Most preferable is ethanol.

The extraction solvent may be preferably used in an amount of from 500 to 5000 parts by weight based on 100 parts by weight of the dry extraction raw material. The extraction temperature is preferably from 40° to 70° C. The extraction may be carried out while allowing the mixture to stand, or while stirring.

Further, in the above-mentioned extraction, it is preferable to repeat the step of extracting an extraction residue again once or more times, because extraction efficiency is improved and yield is improved. The solvent used in the extraction in this case may be the same, or different solvents may be used.

The above-mentioned extract may be used as it is. Alternatively, it is preferable to remove insoluble substances by filtration or centrifugation, because the thrombus formation inhibitory effect is enhanced, so that its application range is widened.

A product prepared by collecting the supernatant (including a soluble fraction) obtained by adding ethanol to an extract as it is or a concentrate after the removal of insoluble substances has an even more enhanced thrombus formation inhibitory effect, and is preferable. The concentration of ethanol is not particularly limited. The final concentration is preferably from 10 to 95% (v/v), more preferably from 60 to 90% (v/v) from the viewpoint of yield and effects.

The extract may be used as it is. Alternatively, the extract may be used by drying into a powder by means such as spray-drying or lyophilization, as desired.

The content of the *gymnema* in the thrombus formation inhibitory agent of the present invention is preferably from 10 to 100% by weight on a dry basis. Taking into consideration convenience of use of the composition, the content is more preferably from 20 to 90% by weight on a dry basis. The content of the extract thereof is preferably from 1 to 100% by weight on a dry basis. Taking into consideration convenience of use of the composition, the content is more preferably from 5 to 95% by weight on a dry basis.

As the thrombus formation inhibitory agent of the present invention, preferable are a thrombus formation inhibitory agent in which an extract of *gymnema* is obtained by extracting *gymnema* with one or more kinds selected from the group consisting of water, bases, acids, and alcohols, and a thrombus formation inhibitory agent in which an extract of *gymnema* is a soluble fraction obtained by further fractionation with ethanol.

The thrombus formation inhibition in the thrombus formation inhibitory agent of the present invention is not particularly limited, and preferably refers mainly to inhibition of thrombus formation caused by anti-platelet aggregation. The anti-platelet aggregation refers to inhibition of the platelet aggregation, and is also simply referred to as anti-platelet. The thrombus formation inhibitory effect can be confirmed as the anti-platelet activity by the method of determining a platelet aggregation ratio with a platelet aggregation analyzer (Aggregometer) when an aggregation-causing substance (ADP, epinephrine, collagen, arachidonic acid or the like) is added to platelet rich plasma or collected blood as shown, for instance, in Test Example E-1 set forth below.

The composition of the present invention can be applied to foodstuff, medicaments, feeds and the like, preferably foodstuff or medicaments which can be easily taken by human. The details of application examples thereof will be described later.

The amount of intake of the composition of the present invention as foodstuff may be properly adjusted depending upon individual cases taking into consideration physical conditions, weight, age, sex and the like of an individual to be administered. The number of times of intake, time periods, timing and the like are not limited, and the foodstuff can be taken once a day or in divided portions of several times a day.

The amount of intake of the composition of the present invention as foodstuff is usually from 0.05 to 20 g/day, preferably from 0.1 to 5 g/day per 50 kg weight of one human individual as the composition.

The dose of the composition of the present invention as the medicament may be properly determined depending upon individual cases taking into consideration an administration method, symptoms of diseases, and weight, age, sex or the like of an individual to be administered and the like. The number of times of intake, time periods, timing and the like are not limited. For instance, the medicament can be administered once a day or in divided portions of several times a day.

The dose of the composition of the present invention as the medicament is usually from about 50 mg to about 2 g/day, preferably from 100 to 500 mg/day per 50 kg weight of one adult individual in terms of the amount of the active ingredient on a dry basis.

(6) Hizikia fusiforme

Specifically, the present invention provides an extrinsic blood coagulation preventing composition, a thrombus preventing composition, and a composition for preventing thrombus, characterized in that each composition comprises, as an active ingredient, *Hizikia fusiforme*, an extract thereof, or a mixture thereof.

The composition of the present invention exhibits its effect based on the action owned by the above-mentioned *Hizikia fusiforme* component. The following action has been found for the *Hizikia fusiforme* component for the first time in the present invention.

In other words, it was seen from the results of the anti-coagulation test for the above-mentioned *Hizikia fusiforme* component that the effect of inhibiting formation of the extrinsic blood coagulation is enhanced.

It was seen from the results of the measurement of an activated partial thromboplastin time (APTT) for the above-mentioned *Hizikia fusiforme* component that the effect of inactivating a factor involved in an intrinsic pathway to inhibit fibrin formation and inhibit thrombus formation in a blood vessel is enhanced.

*Hizikia fusiforme* as used herein has a scientific name of *Hizikia fusiforumis*, and is a seaweed belonging to Phaephyceae, Sargassaceae. This is endemic to Japanese adjacent seas, and is distributed in the Pacific coast, south of Hidaka district of Hokkaido, the Inland Sea of Japan, west of near Hyogo-prefecture of Japan Sea side, and the Kyushu coast. *Hizikia fusiforme* is dark brown when dry, and is yellowish brown when it is raw. *Hizikia fusiforme* is grown on a reef of an open sea where waves are rough, and near a low tidal line, a body is dense green brown, a root is entangled, fibrous and well developed, and is grown while crawling on a rock. A stem of a body is cartilaginous and cylindrical, and has a thickness of 3 to 4 mm and a length of 0.5 to 1 mm, an elongate cylindrical leaf and a small branch are coming out from a side of a stem, a leaf is succulent and flat at a young stage, a leaf becomes a streamline and is 3 to 10 cm at an adult stage, a tip is pointed in many cases, and an interior of a leaf is solid but the leaf becomes a rod-like shape with its tip inflating frequently, or a leaf is hollow and also contains a bubble in some cases, and *Hizikia fusiforme* is grown dense in spring to summer. *Hizikia fusiforme* has much bitterness, and cannot be eaten as in a raw state, but the bitterness is removed by boiling in water in an iron kettle for several hours, and its dye also being removed. When the product is dried with sunshine, it is called "dried *Hizikia fusiforme*." Among dried *Hizikia fusiforme*, a collection of only small branches is "Me-Hijiki, Kome-Hijiki or Hime-Hijiki," a stem-like long portion (portion of major axis) is called "Naga-(long) Hijiki." When Me-Hijiki is recovered by immersing the dry product in water, a volume increase as much as 3-folds, and a weight increases about 6-folds. As a different name, *Hizikia fusiforme* is called as Hizukimo, Neili, Chousen-Hijiki, Michi-Hijiki or the like.

In the present invention, the portion of *Hizikia fusiforme* is not particularly limited, and small branch portions and portions of the major axis are preferably used. Its form is not particularly limited, and any of raw *Hizikia fusiforme*, sun-dried *Hizikia fusiforme*, dried *Hizikia fusiforme*, *Hizikia fusiforme* powder or the like may be used.

In the case of the *Hizikia fusiforme* powder, the powder may be used as it is. It is preferable to remove water-insoluble components by extraction because the powder contains water-insoluble components.

When raw *Hizikia fusiforme*, sun-dried *Hizikia fusiforme* or dried *Hizikia fusiforme* is used as an extraction raw material during the extraction, it is preferable to use a raw material obtained by pulverizing and mixing thoroughly with a mixer or the like for the purpose of enhancing extraction efficiency.

When sun-dried *Hizikia fusiforme* or dried *Hizikia fusiforme* is used as an extraction raw material, it is preferable to use a product obtained by pulverizing a raw material to a particle size of 40 mesh or smaller for the purpose of enhancing extraction efficiency.

The extraction method is not particularly limited in the extraction solvent, the extraction temperature and the like. As the extraction solvent, water, a base, an acid, a hydrophilic solvent or acetone can be used. As the hydrophilic solvent, one or more kinds selected from the group consisting of lower alcohols such as methyl alcohol, ethyl alcohol, n-propylalcohol, isopropyl alcohol and butyl alcohol are preferable from the viewpoint of operability and extraction efficiency. Especially preferable is at least one kind selected from the group consisting of water, bases, acids and hydrophilic solvents.

When the acid or base is used as the extraction solvent, it is preferable to neutralize the extract. A salt formed by a neutralization reaction can be removed by a known method such as a dialysis method and gel filtration. When water is used as the extraction solvent, since the neutralization reaction as mentioned above is not necessary, and removal of the formed salt is not necessitated, it is further preferable to use water.

The acid used during the extraction is not particularly limited, and most of acids can be used. Preferably, one kind selected from hydrochloric acid and sulfuric acid, or a combination of both may be used, from the viewpoint of easy availability and operability.

Also, the base is not particularly limited, and most of bases can be used. Preferably, one kind selected from sodium hydroxide and potassium hydroxide, or a combination of both may be used.

The concentration of the acid or base used in the extraction is not particularly limited, and varies depending upon the strength of the acid or base. It is preferable that the acid or base is used in a concentration of from 0.01 to 0.5 molars from the viewpoint of operability and extraction efficiency. Usually, the acid or base is used in the form of an aqueous solution having the concentration.

The extraction solvent may be preferably used in an amount of from 500 to 5000 parts by weight based on 100 parts by weight of the dry extraction raw material. The extraction temperature is preferably from 40° to 70° C. The extraction may be carried out while allowing the mixture to stand, or while stirring.

In the above-mentioned extraction, it is preferable to perform enzymatic treatment because its yield and flavor can be improved and one having a high efficiency can be obtained with the treatment. The pH for the enzymatic treatment can be properly selected using, as an index, an optimal pH and a pH stability of the enzyme to be used. In addition, the temperature during the treatment can be properly selected using, as an index, an optimal temperature and a temperature stability of the enzyme. The enzyme used in the enzymatic treatment in the present invention is not limited, as long as the enzyme may be used in food industries. One kind selected from pectinase, cellulase, hemicellulase, α-amylase, glucoamylase, maltotrohydrolase, β-amylase, transglucosidase, lipase, protease, glutaminase, nuclease, deaminase, dextranase, glucose oxidase, lactase, tannase, chlorogenic acid esterase, pullulanase, trypsin, papain, rennet, phospholipase $A_2$ and the like, or a combination of two kinds may be used. Preferably, one kind selected from pectinase, cellulase, hemicellulase, protease, chlorogenic acid esterase and tannase, or a combination of two kinds of them may be used. The amount of the enzyme to be used is not particularly limited, and is different depending upon the kinds of enzymes and reaction conditions. It is preferable that the enzyme is used in an amount of from 0.05 to 2 parts by weight based on 100 parts by weight of the dry extraction raw material.

Further, in the above-mentioned extraction, it is preferable to repeat the step of extracting the extraction residue again once or more times because the extraction ratio is improved and the yield is improved. The solvent used in the extraction in this case may be the same, or different solvents may be used.

The extract may be used as it is. It is preferable to remove insoluble substances and a solvent by filtration, centrifugation or fractional distillation, because the extrinsic blood coagulation preventing effect or thrombus preventing effect is enhanced, so that an application range is widened.

After removal of insoluble substances and a solvent, the extract as it is, or a concentrate thereof may be distributed with an organic solvent, and each of the solvent-soluble fractions may be obtained. These solvent-soluble fractions are preferable because they have a further enhanced extrinsic blood coagulation preventing effect or thrombus preventing effect. As the organic solvent, a lower alcohol such as methyl alcohol, ethyl alcohol, n-propyl alcohol, isopropyl alcohol and butyl alcohol, ethyl acetate, butyl acetate, diethyl ether, methyl ether, methyl isobutyl ketone, hexane, acetone or chloroform can be preferably used. It is more preferable to use ethyl alcohol. In order to increase purity of the soluble fraction, the distribution with other hydrophobic solvent may be combined. The concentration of these solvents is not particularly limited. The final concentration is preferably from 20 to 80% (v/v), more preferably from 20 to 60% (v/v), from the viewpoint of yield and effect.

The purification with chromatography or column using a phenolic, styrenic, acrylic acid-based, epoxy amine-based, pyridine-based or methacrylic hydrophobic resin as a matrix may be carried out for the purpose of further enhancing purity. In this case, as an eluent after resin adsorption, a lower alcohol such as methyl alcohol, ethyl alcohol, n-propyl alcohol, isopropyl alcohol or butyl alcohol, and acetone can be used alone, or in the form of an aqueous solution.

The extract and the fraction may be used as they are. Alternatively, the extract and the fraction may be used by drying into a powder by means such as spray-drying or lyophilization, as desired.

The content of *Hizikia fusiforme* in the extrinsic blood coagulation preventing composition, the thrombus preventing composition or the composition for preventing thrombus of the present invention is preferably from 10 to 100% by weight on a dry basis. Taking into consideration convenience of use of the composition, the content is more preferably from 20 to 90% by weight on a dry basis. The content of an extract thereof is preferably from 1 to 100% by weight on a dry basis. Taking into consideration convenience of use of the composition, the content is more preferably from 5 to 95% by weight on a dry basis.

As the extrinsic blood coagulation preventing composition, the thrombus preventing composition or the composition for preventing thrombus of the present invention, preferable are a composition in which a *Hizikia fusiforme* extract is obtained by extracting *Hizikia fusiforme* with at least one kind selected from the group consisting of water, bases, acids, hydrophilic solvents and acetone, and a composition containing a fraction fractionated with an organic solvent, preferably at least one kind selected from the group consisting of methyl alcohol, ethyl alcohol, n-propyl alcohol, isopropyl alcohol, butyl alcohol, ethyl acetate, butyl acetate, diethyl ether, methyl ether, methyl isobutyl ketone, hexane and chloroform of a *Hizikia fusiforme* extract. The extract is more preferably subjected to an enzymatic treatment.

The extrinsic blood coagulation preventing effect in the extrinsic blood coagulation preventing composition of the present invention can be confirmed by measuring a prothrombin time (PT) which is a method of assaying the anti-blood coagulant activity for the extrinsic blood coagulation system as shown, for instance, in Test Example F-1 set forth below.

The thrombus preventing effect in the thrombus preventing composition and the composition for preventing thrombus of the present invention can be confirmed, for instance, by measuring an activated partial thromboplastin time (APTT)

which is a method of measuring anti-blood coagulant activity for the intrinsic blood coagulation system. For instance, as to the thrombus preventing composition of the present invention, the effect can be confirmed in accordance with Test Example F'-1 set forth below, and as to the composition for preventing thrombus of the present invention, the effect can be confirmed in accordance with Test Example F'''-1 set forth below, respectively.

The composition of the present invention can be applied to foodstuff, medicaments, feeds and the like, preferably foodstuff or medicaments which can be easily taken by human. The details of application examples thereof will be described later.

The amount of intake of the composition of the present invention as foodstuff may be properly adjusted depending upon individual cases taking into consideration physical conditions, weight, age, sex and the like of an individual to be administered. The number of times of intake, time periods, timing and the like are not limited, and the foodstuff can be taken once a day or in divided portions of several times a day.

The amount of intake of the composition of the present invention as foodstuff is usually from 0.05 to 20 g/day, preferably from 0.1 to 5 g/day per 50 kg weight of one human individual as the composition.

The dose of the composition of the present invention as the medicament may be properly determined depending upon individual cases taking into consideration an administration method, symptoms of diseases, and weight, age, sex or the like of an individual to be administered. The number of times of administration, time periods, timing and the like are not limited. For instance, the medicament can be administered once a day or in divided portions of several times a day.

The dose of the extrinsic blood coagulation preventing composition of the present invention as the medicament is usually from about 50 mg to about 2 g/day, preferably from 100 to 500 mg/day per 50 kg of one adult individual, in terms of the amount of the active ingredient, on a dry basis.

The dose of the thrombus preventing composition and the composition for preventing thrombus of the present invention as the medicament is usually from about 1 to about 40 mg/day, preferably from 2 to 10 mg/day per 50 kg weight of one adult individual expressed in terms of the amount of an active ingredient on a dry basis.

(7) Carrageenan

Specifically, the present invention provides an antithrombotic agent, characterized in that the agent comprises carrageenan as an active ingredient.

The composition of the present invention exhibits its effect based on the action owned by carrageenan. The following action has been found for the carrageenan for the first time in the present invention.

Specifically, it was seen from the results of the measurement of an activated partial thromboplastin time (APTT) for the above-mentioned carrageenan component that the effect of inactivating a factor involved in an intrinsic pathway to inhibit fibrin formation and inhibit thrombus formation in a blood vessel is enhanced.

Carrageenan used in the present invention is a natural macromolecular substance obtained by extraction and purification from a seaweed such as *Hypnea charoides* Lamouroux, *Eucheuma, Iridaea, Chondracanthus tenellus* Hommersand or *Chondrus ocellatus* Holmes, and is a polysaccharide having a molecular weight of from 100000 to 500000 and containing galactose and 3,6-anhydrogalactose as a main component.

Commercially available carrageenan can be used, and preferably, carrageenan is one obtained by once dissolving in water or hot water, filtering the solution obtained, and removing insoluble components.

As to the kinds of carrageenan, any of ι-carrageenan, κ-carrageenan and λ-carrageenan may be used, or a combination of a plurality of them may be used. One kind of ι-carrageenan and λ-carrageenan or a combination of a plurality of them is preferable from the viewpoint of the effect, and λ-carrageenan is further preferable.

The content of carrageenan in the antithrombotic agent of the present invention is preferably from 1 to 100% by weight on a dry basis. Taking into consideration convenience of use of the composition, the content is more preferably from 5 to 95% by weight on a dry basis.

The anti-thrombus in the present invention is not particularly limited, and preferably refers to an action of inhibiting thrombus formation (anti-coagulant action). The anti-thrombus effect can be confirmed by measuring an activated partial thromboplastin time (APTT) in the method for assaying the anti-coagulant activity on the intrinsic blood coagulation system as shown, for instance, in Test Example G-1 set forth below.

The composition of the present invention can be applied to foodstuff, medicaments, feeds and the like, preferably foodstuff or medicaments which can be easily taken by human. The details of application examples thereof will be described later.

The amount of intake of the composition of the present invention as foodstuff may be properly adjusted depending upon individual cases taking into consideration physical conditions, weight, age, sex and the like of an individual to be administered. The number of times of intake, time periods, timing and the like are not limited, and for instance, the foodstuff can be taken once a day or in divided portions of several times a day.

The amount of intake of the composition of the present invention as foodstuff is usually from 0.05 to 20 g/day, preferably from 0.1 to 5 g/day per 50 kg weight of one human individual as the composition.

The dose of the composition of the present invention as the medicament may be properly determined depending upon individual cases taking into consideration an administration method, symptoms of diseases, and weight, age, sex or the like of an individual to be administered. The number of times of administration, time periods, timing and the like are not limited. For instance, the medicament can be administered once a day or in divided portions of several times a day.

The dose of the composition of the present invention as the medicament is usually from about 50 mg to about 2 g/day, preferably from 100 to 500 mg/day per 50 kg weight of one adult individual in terms of the amount of the active ingredient on a dry basis.

Examples of components other than the active ingredient of the present invention in the composition for inhibiting thrombus formation of the present invention described in the above (1) to (7) include known food raw material components such as polysaccharides such as dextrin, cyclic dextrin, cluster dextrin, hardly-digestible dextrin, xanthane, guar, guar gum degradation product, and alginic acid; a vegetable protein such as soybean protein; a degradation product of a vegetable protein such as soybean peptide; an animal protein such as yolk, egg white, and whole egg; and a degradation product of an animal protein such as yolk, egg white and whole egg peptide; lactose and the like. The composition of the present invention can be prepared by properly mixing those known components and the active ingredient of the present invention. The above-mentioned components may be natural or synthetic product.

(8) Application Examples of Compositions of the Present Invention

One embodiment of the present invention provides foodstuff comprising the composition for inhibiting thrombus formation of the present invention. The composition for inhibiting thrombus formation means any of the above-mentioned compositions of the present invention.

The foodstuff in the present invention are not particularly limited as long as they have the form capable of being orally taken such as solutions, suspensions, powders and solid molded products. Usually, the content of the composition for inhibiting thrombus formation of the present invention is preferably from 0.01 to 15% by weight, more preferably from 0.05 to 10% by weight of the foodstuff. The foodstuff as described above can be prepared according to a known formulation composition of and a known preparation process of the foodstuff except that the composition for inhibiting thrombus formation of the present invention is blended as a part of the raw material.

More specifically, the foodstuff in the present invention are exemplified by instant foods such as instant noodles, retort pouched foods, canned foods, microwave-cooking foods, instant soups and miso soups, and freeze-dried foods; beverages such as soft drinks, fruit juice beverages, vegetable juice beverages, soya milk beverages, coffee beverages, tea beverages, powder beverages, concentrated beverages, nutritious beverages, and alcoholic beverages; wheat flour products such as bread, pastas, noodles, cake mix, deep frying powder, and bread crumbs; confectionaries such as candies, caramels, chewing gums, chocolates, cookies, biscuits, cakes, pies, snacks, crackers, Japanese confectionaries, and dessert confectionaries; seasonings such as sauces, tomato-processed seasonings, flavor seasonings, culinary mix, gravy sauces, dressings, soups, and roux for curry sauce and stew; fats and oils such as processed fats and oils, butter, margarine, and mayonnaise; milk products such as milk beverages, yogurts, lactobacilli beverage, ice creams, and creams; processed marine products such as frozen foods, hams and sausages made of fish meat, and marine pastes; livestock processed products such as livestock hams and sausages; agricultural processed products such as agricultural canned foods, jams and marmalades, pickles, cooked beans, and cereals; nutritional foods; tablets; capsules; and the like.

Various nutritional components can be enriched in the composition for inhibiting thrombus formation of the present invention, or foodstuff containing the composition.

The nutritional component that can be enriched in the composition is not particularly limited. There can be used one kind selected from a vitamin such as vitamin A, vitamin $B_1$, vitamin $B_2$, vitamin $B_6$, vitamin $B_{12}$, vitamin C, vitamin D, vitamin E, niacin (nicotinic acid), pantothenic acid, or folic acid; an essential amino acid such as lysine, threonine, or tryptophan; a mineral such as calcium, magnesium, iron, zinc, or copper; substances which contribute to human health, for instance, α-linolenic acid, EPA, DHA, evening primrose oil, octacosanol, caseinphosphopeptide (CPP), caseincalciumpeptide (CCP), water-soluble dietary fibers, insoluble dietary fibers, oligosaccharides and the like; and other useful substances approved as foods and food additives, or two more kinds thereof.

In addition, one embodiment of the present invention provides a quasi-drug and a medicament, each comprising the composition for inhibiting thrombus formation of the present invention. The composition for inhibiting thrombus formation means any of the above-mentioned compositions of the present invention.

The quasi-drug and the medicament according to the present invention can be prepared, for instance, as an oral preparation or an injectable, by blending an excipient which is suitable for oral or parenteral administration, other additives and the composition for inhibiting thrombus formation of the present invention according to the conventional method. Preferable is an oral preparation such as an oral solid preparation and an oral liquid preparation, and most preferable is an oral solid preparation which can be easily taken, which is suitable for storage and carrying. Usually, the content of the composition for inhibiting thrombus formation of the present invention is preferably from 0.1 to 300% by weight, more preferably from 1 to 100% by weight, of the quasi-drug or the medicament.

Examples of the oral solid preparation include tablets, powders, fine granules, granules, capsules, pills, sustained-release preparations and the like. The solid preparation as mentioned above can be prepared in the form of a tablet, a powder, a fine granule, a granule, a capsule, a pill, a sustained-release agent or the like by properly mixing a carrier, an excipient (for instance, starch, lactose, white sugar, calcium carbonate, calcium phosphate and the like), a binder (for instance, starch, gum arabic, carboxymethyl cellulose, hydroxypropyl cellulose, crystalline cellulose, alginic acid, gelatin, polyvinyl pyrrolidone and the like), a lubricant (for instance, stearic acid, magnesium stearate, calcium stearate and the like), and a disintegrating agent (for instance, carboxymethyl cellulose, talc and the like) which are pharmaceutically acceptable, and the composition for inhibiting thrombus formation of the present invention according to a conventional method.

The oral liquid preparation includes pharmaceutically acceptable emulsions, solutions, suspensions, syrups, elixirs and the like, and contains an inert diluent which is generally used such as purified water or ethyl alcohol. The preparation may contain, in addition to the inert diluent, a wetting agent, a supplementing agent such as a suspending agent, a sweetener, a flavor, an aromatic agent or an antiseptic.

The injectable for parenteral administration includes sterile aqueous or non-aqueous solutions, suspensions, and emulsions. The diluent for aqueous solutions and suspensions includes, for instance, distilled water for injection and physiological saline. The diluent for non-aqueous solutions or suspensions includes, for instance, propylene glycol, polyethylene glycol, vegetable oils such as olive oil, alcohols such as ethyl alcohol, Polysorbate 80 and the like. The injectable may further contain an supplementing agent such as an antiseptic, a wetting agent, an emulsifier, a dispersant, a stabilizer (for instance, lactose), or a solubilizing aid (for instance, glutamic acid and aspartic acid). These injectables are sterilized by, for instance, filtration through a bacteria capturing filter, formulation of a sterilizing agent or irradiation. These injectables may be also used by preparing a sterile solid composition, and dissolving the composition in sterile water or a sterile solvent for injection before use.

Further, one embodiment of the present invention provides a feed comprising the composition for inhibiting thrombus formation of the present invention. The composition for inhibiting thrombus formation means any of the above-mentioned compositions of the present invention.

The feed according to the present invention can be prepared according to a known blending composition of and a process for preparing a feed except that the composition for inhibiting thrombus formation of the present invention is blended as a part of the raw material. Usually, the content of the composition for inhibiting thrombus formation of the present invention is preferably from 0.01 to 15% by weight, more preferably from 0.05 to 10% by weight, of the feed.

The organism to which the feed can be applied is not particularly limited. The organism includes, for instance, a culturing or breeding animal, a pet animal and the like. The culturing or breading animal includes cattle such as *Equus, Bos, Porcus, Ovis, Capra, Camelus* and *Lama*; experimental animals such as mice, rats, guinea pigs and rabbits; poultry such as *Chrysolophus*, ducks, *Meleagris* and *Struthioniformes*; and the pet animals includes dogs, cats and the like.

In the present invention, a plant body, or fruit, leaf or seed thereof is used as an active ingredient. These portions are directly used as they are. Alternatively, they are used in various forms obtained by carrying out physical treatment according to a known method, such as dry products, smashed products, and pulverized products. Therefore, in the present invention, the form obtained after the physical treatment mentioned above is also handled as a plant body, fruit, leaf or seed thereof. In addition, the plant body, fruit, leaf or seed thereof after the physical treatment mentioned above alone or two or more kinds of them are mixed with, for instance, a polysaccharide such as dextrin, cyclic dextrin, cluster dextrin, hardly-digestible dextrin, xanthan, guar, guar gum degradation product, or alginic acid; a vegetable protein such as a soybean protein; a degradation product of a vegetable protein such as a soybean peptide; an animal protein such as yolk, egg white, or whole egg; a degradation product of an animal protein such as yolk, egg white, or whole egg peptide, an excipient such as lactose; a binder such as starch, cellulose, gum arabic, or glucose, a disintegrating agent such as gelatin, agar, or cellulose; and a lubricant such as magnesium stearate, sugar esters, or a glycerol fatty acid ester, and is solidified, which is also encompassed in the composition, the foodstuff, the quasi-drug, the medicament and the feed of the present invention.

Since the above-mentioned foodstuff and the like which are an application example of the composition of the present invention contain the composition for inhibiting thrombus formation of the present invention, they can exhibit the thrombus formation inhibitory effect owing to the function and effects exhibited by individual compositions of the present invention.

EXAMPLES

The present invention will be specifically described hereinbelow by the Examples, without intending to limit the scope of the present invention thereto. Examples will be shown for each plant which is a source of a plant component used as an active ingredient.

Amla

Example A-1

Preparation 1 of Antithrombotic Composition

A dry fruit of amla was pulverized to a size of 40 mesh or smaller, and 2 liters of distilled water was added to 80 g of the powder, and the mixture was subjected to extraction at 55° C. for 3 hours. Thereafter, the resulting mixture was centrifuged, and the supernatant was filtered to separate into an extract and residue. Two liters of distilled water was added to the residue, and the mixture was subjected to extraction once again under the same conditions. Each of the extracts was combined to give an antithrombotic composition A of the present invention.

Here, the extract obtained was 70.8 g calculated as a solid content, and its yield was 88.5%.

Test Example A-1

Confirmation of Antithrombotic Effects

The anti-coagulant activity of the antithrombotic composition of the present invention was assayed with Coagulometer (manufactured by SYSMEX CORPORATION) utilizing platelet poor plasma (PPP) separated from human blood.

Ten microliters of a sample, 25 microliters of an APTT reagent (manufactured by INTERNATIONAL REAGENTS CORPORATION) and 25 microliters of 10% cephalin were placed in a reaction cuvette to react the components at 37° C. for 3 minutes. Thereafter, 50 microliters of PPP was added thereto to react the components for 2 minutes. Finally, 50 microliters of 25 millimolar calcium chloride was added to the mixture obtained to coagulate the mixture. The time period (seconds) by which the plasma was coagulated was measured, and defined as APTT.

At this point, water was added as the control, and the APTT was measured in the same manner. The anti-coagulant activity (%) against the control was calculated from APTT of the measured sample according to the numerical formula.

Anti-Coagulant Activity(%)=(($APTT$ of Sample–$APTT$ of Control)/$APTT$ of Control)×100

In order to confirm the relationship between the concentration of the antithrombotic composition A of the present invention and the anti-coagulant activity, the activity was assayed using the antithrombotic composition of the present invention of which amount was 0 (control), 1, 3 or 5 mg/mL calculated as a solid content concentration. The results are shown in Table 1 given below.

TABLE 1

| Concentration | APTT (second) | Anti-Coagulant Activity (%) |
| --- | --- | --- |
| 0 mg/mL | 45 | 0 |
| 1 mg/mL | 49 | 8.9 |
| 3 mg/mL | 55 | 22.2 |
| 5 mg/mL | 68 | 51.1 |

It could be confirmed from the results of Table 1 mentioned above that the antithrombotic composition of the present invention exhibits a high anti-coagulant activity. It could be also confirmed that anti-coagulant activity is increased proportionally to the increase in the concentration of the extract.

Example A-2

Preparation 2 of Antithrombotic Composition

A dry fruit of amla was pulverized to a size of 40 mesh or smaller, and 2 liters of distilled water was added to 80 g of the powder, and the mixture was subjected to extraction at 55° C. for 3 hours. Thereafter, the resulting mixture was centrifuged, and the supernatant was filtered to separate into an extract and residue. Two liters of distilled water was added to the residue, and the mixture was subjected to extraction once again under the same conditions. Each of the extracts was combined, and the combined extract was concentrated under reduced pressure condition to a volume of 200 milliliters. Ethanol was added to the concentrate so as to make up a volume of 1 liter (final ethanol concentration: 80%), and thereafter the solution was allowed to stand at room temperature for 24 hours to precipitate insoluble components. The precipitates were separated by centrifugation, and dried under reduced pressure condition. The residue was then re-dissolved in 1 liter of water, and the mixture was filtered to remove insoluble components. Thereafter, the filtrate was lyophilized to give an antithrombotic composition B: 30.8 g (yield: 38.5%) of the present invention.

Test Example A-2

Confirmation of Antithrombotic Effect

The APTT was measured for the antithrombotic composition B obtained in Example A-2 in the same manner as in Test Example A-1 at a concentration of 5 mg/mL. As a result, it was confirmed that the APTT was 85.1 seconds, and the anti-coagulant activity was 89.1%, demonstrating a higher anti-coagulant activity as compared to the antithrombotic composition A obtained by extraction with water alone.

The APTT was also measured for the ethanol-soluble component in Example A-2. As a result, the APTT was 48.0 seconds, and the anti-coagulant activity was 6.7%, whereby it could be seen that the antithrombotic active fraction is contained in the precipitated fraction with ethanol.

Example A'-1

Preparation 1 of Fibrin Formation Inhibitory Composition

A dry fruit of amla was pulverized to a size of 40 mesh or smaller, and 2 liters of distilled water was added to 80 g of the powder, and the mixture was subjected to extraction at 55° C. for 3 hours. Thereafter, the resulting mixture was centrifuged (3000 rpm, 10 minutes), and the supernatant was filtered to separate into an extract and residue. Two liters of distilled water was added to the residue, and the mixture was subjected to extraction once again under the same conditions. Each of the extracts was combined, and the combined extract was lyophilized to give a fibrin formation inhibitory composition A: 35.0 grams of the present invention. Its yield was 43.8%.

Test Example A'-1 Confirmation 1 of Fibrin Formation Inhibitory Effect

Regarding the fibrin formation inhibitory effect of the fibrin formation inhibitory composition of the present invention, the ratio of fibrin formation was examined utilizing a fibrinogen test solution and a thrombin test solution.

In a test tube, 300 microliters of a solution prepared by diluting the fibrin formation inhibitory composition A obtained in Example A'-1 with a physiological saline to a given concentration was added to 3 milliliters of a 0.7% fibrinogen test solution. The mixture was mixed thoroughly at 37° C. for 3 minutes, and 300 microliters of a thrombin test solution (10 U/mL) was added thereto to form and coagulate fibrin. The weight (g) of the coagulate was determined, and the fibrin formation inhibitory ratio was calculated according to the following calculation formula.

Fibrin Formation Inhibitory Ratio(%)=((Weight of Entire Solution−Weight of Coagulate)/Weight of Entire Solution)×100

Here, as the control, a physiological saline was used in place of the fibrin formation inhibitory composition, and the fibrin formation inhibitory ratio was determined in the same manner.

In order to confirm the relationship between the concentration of the fibrin formation inhibitory composition of the present invention and the fibrin formation inhibitory ratio, the inhibitory ratio was determined using the fibrin formation inhibitory composition of the present invention of which amount was 0 (control), 10, 25 or 40 mg/mL calculated as a solid content concentration. The results are shown in Table 2 given below.

TABLE 2

| Concentration | Weight (g) of Coagulate | Fibrin Formation Inhibitory Ratio (%) |
| --- | --- | --- |
| 0 mg/mL | 3.65 | 0 |
| 10 mg/mL | 2.37 | 31.2 |
| 25 mg/mL | 1.14 | 64.9 |
| 40 mg/mL | 0 | 100 |

It could be confirmed from the results of Table 2 mentioned above that the fibrin formation inhibitory composition of the present invention shows a high inhibitory effect on the fibrin formation during final process of thrombus formation. In addition, it could be confirmed that the fibrin formation inhibitory ratio is increased proportionally to the increase in the concentration of the extract.

Example A'-2 Preparation 2 of Fibrin Formation Inhibitory Composition

A dry fruit of amla was pulverized to a size of 40 mesh or smaller, and 2 liters of distilled water was added to 100 g of the powder, and 0.1 grams of pectinase and 0.1 grams of tannase were further added thereto, and the mixture was subjected to extraction at 55° C. for 2 hours. Thereafter, the enzymes were deactivated at 90° C. for 30 minutes. Subsequently, the mixture was centrifuged (3000 rpm, 10 minutes), and the supernatant was filtered. The filtrate was spray-dried to give a fibrin formation inhibitory composition B: 45 g of the present invention.

Example A'-3 Preparation 3 of Fibrin Formation Inhibitory Composition

A dry fruit of amla was pulverized to a size of 40 mesh or smaller, and 2 liters of distilled water was added to 80 g of the powder, and the mixture was subjected to extraction at 55° C. for 3 hours. Thereafter, the resulting mixture was centrifuged (3000 rpm, 10 minutes), and the supernatant was filtered to separate into an extract and residue. Two liters of distilled water was added to the residue, and the mixture was subjected to extraction once again under the same conditions. Each of the extracts was combined, and the combined extract was concentrated under reduced pressure condition to a volume of 200 milliliters. Ethanol was added to the concentrate so as to make up a volume of 250 milliliters (final ethanol concentration: 20%). Thereafter, the mixture was allowed to stand at 4° C. for 24 hours to precipitate insoluble components. The supernatant was separated and removed by centrifugation (3000 rpm, 10 minutes), and the precipitates were lyophilized to give a fibrin formation inhibitory composition C: 8.5 g of the present invention.

In addition, ethanol was added to the supernatant having a final ethanol concentration of 20% so as to give a final ethanol concentration of 40% to form precipitates, to give a fibrin formation inhibitory composition D: 4.6 g of the present invention in the same manner. Further, the same procedures were repeated, so as to give a final ethanol concentration of 60%, and further 80%, to give fibrin formation inhibitory compositions E: 1.3 g and F: 2.4 g of the present invention as the precipitates.

Test Example A'-2

Confirmation 2 of Fibrin Formation Inhibitory Effect

Each of the fibrin formation inhibitory composition B obtained in Example A'-2 and the fibrin formation inhibitory compositions C to F obtained in Example A'-3 was diluted in a physiological saline so as to have a sample concentration of 10 mg/mL, and the fibrin formation inhibitory effect was confirmed in the same manner as in Test Example A'-1.

In addition, regarding the 60-80% ethanol supernatant component in Example A'-3, the sample was prepared, and the fibrin formation inhibitory effect was confirmed in the same manner. The results are shown in Table 3.

TABLE 3

| Sample | Weight of Coagulate (g) | Fibrin Formation Inhibitory Effect (%) |
|---|---|---|
| 0 mg/mL | 3.65 | 0 |
| Fibrin Formation Inhibitory Composition B | 2.14 | 41.4 |
| Fibrin Formation Inhibitory Composition C (0-20% Ethanol-Precipitated Component) | 2.01 | 44.9 |
| Fibrin Formation Inhibitory Composition D (20-40% Ethanol-Precipitated Component) | 2.34 | 35.9 |
| Fibrin Formation Inhibitory Composition E (40-60% Ethanol-Precipitated Component) | 1.32 | 63.8 |
| Fibrin Formation Inhibitory Composition F (60-80% Ethanol-Precipitated Component) | 0 | 100 |
| 60-80% Ethanol Supernatant Component | 2.82 | 22.7 |

It could be seen from the results of Table 3 mentioned above that the fibrin formation inhibitory fractions have the highest activity in the 60-80% ethanol-precipitated fraction of the ethanol-precipitated fractions.

Example A'-1

Preparation 1 of Anti-Platelet Aggregation Composition

A dry fruit of amla was pulverized to a size of 40 mesh or smaller, and 2 liters of distilled water was added to 80 g of the powder, and the mixture was subjected to extraction at 55° C. for 3 hours. Thereafter, the resulting mixture was centrifuged, and the supernatant was filtered to separate into an extract and residue. Two liters of distilled water was added to the residue, and the mixture was subjected to extraction once again under the same conditions. Each of the extracts was combined, and the combined extract was then lyophilized to give an anti-platelet aggregation composition A: 35 g of the present invention.

Test Example A"-1

Confirmation of Anti-Platelet Activity

The anti-platelet activity of the anti-platelet aggregation composition of the present invention was obtained in the following manner. Eighty microliters of a sample was added to 400 μL of platelet rich plasma of a normal individual, and 20 μL of ADP (1 mg/mL solution) was then added thereto as an aggregation-causing substance. The platelet aggregation ratio after 5 minutes was determined by using a platelet aggregation analyzer (Aggregometer, manufactured by ISK).

Separately, as the control, water (sample concentration: 0 mg/mL) was added, and the platelet aggregation ratio was determined in the same manner. The anti-platelet activity (%) was calculated from the determined platelet aggregation ratio, relative to that of the control according to the following numerical formula.

Anti-Platelet Activity(%)=((Platelet Aggregation Ratio of Control−Platelet Aggregation Ratio When Adding Sample)/Platelet Aggregation Ratio of Control)×100

The results determined at a sample concentration of 2.5, 5.0 or 7.5 mg/mL are shown in Table 4.

TABLE 4

| Sample Concentration | Anti-Platelet Activity (%) |
|---|---|
| 2.5 mg/mL | 24.4 |
| 5.0 mg/mL | 37.8 |
| 7.5 mg/mL | 53.7 |

It could be confirmed from the results of Table 4 mentioned above that the anti-platelet aggregation composition of the present invention shows a high anti-platelet activity. In addition, it could be confirmed that anti-platelet activity is increased proportionally to the increase in the concentration of the extract.

Example A"-2

Preparation 2 of Anti-Platelet Aggregation Composition

A dry fruit of amla was powered to a size of 40 mesh or smaller, and 2 liters of distilled water was added to 80 g of the powder, and the mixture was subjected to extraction at 55° C. for 3 hours. Thereafter, the resulting mixture was centrifuged, and the supernatant was filtered to separate into an extract and residue. Two liters of distilled water was added to the residue, and the mixture was subjected to extraction once again under the same conditions. Each of the extracts was combined, and the combined extract was concentrated under reduced pressure condition to a volume of 200 milliliters. Ethanol was added to the concentrate so as to make up a volume of 250 milliliters (final ethanol concentration: 20%), and the mixture was allowed to stand at 4° C. for 24 hours to precipitate insoluble components. The precipitates were separated and removed by centrifugation. The supernatant was dried under reduced pressure condition, the residue was re-dissolved in 1 liter of water, and the solution was filtered to remove insoluble components. Thereafter, the filtrate was lyophilized to give an anti-platelet aggregation composition B: 29 g of the present invention.

In the same manner, the anti-platelet aggregation compositions C, D and E of the present invention were obtained in amounts of 27 g, 26 g and 25 g, respectively by adjusting the final ethanol concentrations to 40%, 60% and 80%.

Test Example A"-2

Confirmation of Anti-Platelet Activity

The anti-platelet activities were assayed for the anti-platelet aggregation compositions B to E obtained in Example A"-2 at a sample concentration of 5.0 mg/mL in the same manner as in Test Example A"-1.

In addition, a sample was prepared for an 80% ethanol-precipitated fraction in Example A"-2, and its anti-platelet activity was assayed in the same manner. The results are shown in Table 5.

TABLE 5

| Sample | Anti-Platelet Activity (%) |
|---|---|
| Anti-Platelet Aggregation Composition B (20% Ethanol-Soluble Fraction) | 52.4 |
| Anti-Platelet Aggregation Composition C (40% Ethanol-Soluble Fraction) | 29.3 |
| Anti-Platelet Aggregation Composition D (60% Ethanol-Soluble Fraction) | 42.7 |
| Anti-Platelet Aggregation Composition E (80% Ethanol-Soluble Fraction) | 39.0 |
| 80% Ethanol-Precipitated Fraction | 1.2 |

It could be seen from the results of Table 5 mentioned above that the anti-platelet active fraction is contained in the ethanol-soluble fraction, and that the fraction from which the precipitates were removed with 20% ethanol has the highest activity.

Example A'''-1

Preparation 1 of Platelet Aggregation Inhibitory Composition

A dry fruit of amla was pulverized to a size of 40 mesh or smaller, and 2 L of distilled water was added to 80 g of the powder, and the mixture was subjected to extraction at 55° C. for 3 hours. Thereafter, the resulting mixture was centrifuged (3000 rpm, 10 minutes), and the supernatant was filtered to separate into an extract and residue. Two liters of distilled water was added to the residue, and the mixture was subjected to extraction once again under the same conditions. Each of the extracts was combined, and the combined extract was lyophilized to give a platelet aggregation inhibitory composition A: 35.0 g of the present invention. Its yield was 43.8%.

Test Example A'''-1

Confirmation 1 of Anti-Platelet Aggregation Activity

The anti-platelet aggregation activity of the platelet aggregation inhibitory composition of the present invention was obtained in the following manner. Five microliters of a sample was added to 200 μL of the blood of a normal individual, 22 μL of ristocetin sulfate (American Biochemical: 100 mg/vial) adjusted so as to have a final concentration of 10 μM was then added thereto as an aggregation-causing substance, and a platelet aggregation ratio after 5 minutes was determined by using a whole blood platelet aggregation analyzer (WBA-Neo, manufactured by ISK).

Separately, as the control, water (sample concentration: 0 mg/mL) was added, and the platelet aggregation ratio was determined in the same manner. The anti-platelet aggregation activity (%) was calculated from the determined platelet aggregation ratio, relative to that of the control according to the following numerical formula.

Anti-Platelet Aggregation Activity(%)=((Platelet Aggregation Ratio of Control−Platelet Aggregation Ratio When Adding Sample)/Platelet Aggregation Ratio of Control)×100

A sample was prepared by diluting the platelet aggregation inhibitory composition A with distilled water so as to have a concentration of 1.25, 2.5 or 5.0 mg/mL. The concentrations of the platelet aggregation inhibitory composition A and the results for assaying the anti-platelet aggregation activity (%) at each concentration are shown in Table 6.

TABLE 6

| Sample Concentration | Platelet Aggregation Inhibitory Composition A |
|---|---|
| 0 mg/mL | 0 |
| 1.25 mg/mL | 26.2 |
| 2.5 mg/mL | 45.1 |
| 5.0 mg/mL | 92.7 |

It was suggested from the results of Table 6 mentioned above that the platelet aggregation inhibitory composition of the present invention has anti-platelet aggregation effect for inhibiting the crosslinking formation between collagen and GpIb by vWF in the platelet aggregation. In addition, it could be confirmed that anti-platelet aggregation activity is increased proportionally to the increase in the concentration of the platelet aggregation inhibitory composition.

Example A'''-2

Preparation 2 of Platelet Aggregation Inhibitory Composition

A dry fruit of amla was pulverized to a size of 40 mesh or smaller, and 2 L of distilled water was added to 80 g of the powder, and the mixture was subjected to extraction at 55° C. for 3 hours. Thereafter, the resulting mixture was centrifuged (3000 rpm, 10 minutes), and the supernatant was filtered to separate into an extract and residue. Two liters of distilled water was added to the residue, and the mixture was subjected to extraction once again under the same conditions. Each of the extracts was combined, and the combined extract was concentrated under reduced pressure condition to a volume of 200 mL. Ethyl alcohol was added to the concentrate so as to make up a volume of 1 L (final ethyl alcohol concentration: 80%). Thereafter, the mixture was allowed to stand at 4° C. for 24 hours to precipitate insoluble components. The precipitates were separated and removed by centrifugation, and the supernatant was concentrated under reduced pressure condition. Thereafter, the concentrate was re-dissolved in 1 L of water, and the solution was filtered to remove insoluble components. Subsequently, the filtrate was lyophilized to give a platelet aggregation inhibitory composition B: 12.5 g (yield: 15.6%) of the present invention.

In the same manner, platelet aggregation inhibitory compositions C: 13.6 g (yield: 17.0%), D: 20.8 g (yield: 26.0%), and E: 21.2 g (yield: 26.5%) of the present invention were obtained, respectively, by adjusting the final ethyl alcohol concentrations to 20%, 40% and 60%.

Example A'''-3

Preparation 3 of Platelet Aggregation Inhibitory Composition

A dry fruit of amla was pulverized to a size of 40 mesh or smaller, and 2 L of distilled water was added to 80 g of the powder, and the mixture was subjected to extraction at 55° C. and 3 hours. Thereafter, the resulting mixture was centrifuged (3000 rpm, 10 minutes), and the supernatant was filtered to separate into an extract and residue. Two liters of distilled water was added to the residue, and the mixture was subjected to extraction once again under the same conditions. Each of the extracts was combined, and the combined extract was lyophilized to give about 37.0 g of a dried product. One liter of ethyl alcohol was added to 35 g of the dry product, and the mixture was allowed to stand at 4° C. for 24 hours to precipitate insoluble components. The precipitates were separated and removed by centrifugation, and the supernatant was concentrated under reduced pressure condition. The residue was re-dissolved in 1 L of water, and filtered to remove insoluble components. Thereafter, the filtrate was lyophilized to give a platelet aggregation inhibitory composition F: 3.5 g of the present invention.

Example A'''-4

Preparation 3 of Platelet Aggregation Inhibitory Composition

A dry fruit of amla was pulverized to a size of 40 mesh or smaller, and 2 L of distilled water was added to 80 g of the powder, and the mixture was subjected to extraction at 55° C. for 3 hours. Thereafter, the resulting mixture was centrifuged, and the supernatant was filtered to separate into an extract and residue. Two liters of distilled water was added to the residue, and the mixture was subjected to extraction once again under the same conditions. Each of the extracts was combined, and the combined extract was concentrated under reduced pressure condition to a volume of 200 mL. Ethyl acetate was added to the concentrate so as to make up a volume of 500 mL (final ethyl acetate concentration: 60%). After the mixture was stirred thoroughly, the mixture was allowed to stand at 4° C. for 24 hours, and the ethyl acetate layer was separated and concentrated under reduced pressure condition. Thereafter, the filtrate was lyophilized to give a platelet aggregation inhibitory composition G: 12.5 g of the present invention.

Example A'''-5

Preparation 4 of Platelet Aggregation Inhibitory Composition

A dry fruit of amla was pulverized to a size of 40 mesh or smaller, and 2 L of distilled water was added to 100 g of the powder. Further, 0.1 g of pectinase and 0.1 g of tannase were added, and the mixture was subjected to extraction at 55° C. for 2 hours. Thereafter, the enzymes were deactivated at 90° C. for 30 minutes. Thereafter, the resulting mixture was centrifuged (3000 rpm, 10 minutes), and the supernatant was filtered, and the filtrate was spray-dried to give a platelet aggregation inhibitory composition H: 45 g of the present invention.

Test Example A'''-2

Confirmation 2 of Anti-Platelet Aggregation Activity

The anti-platelet aggregation activities were calculated by determining the platelet aggregation ratio for the platelet aggregation inhibitory compositions B, C, D and E obtained in Example A'''-2, the platelet aggregation inhibitory composition F obtained in Example A'''-3, the platelet aggregation inhibitory composition G obtained in Example A'''-4, and the platelet aggregation inhibitory composition H obtained in Example A'''-5, each at a concentration of 5.0 mg/mL in the same manner as in Test Example A'''-1. The results are shown in Table 7.

TABLE 7

| Platelet Aggregation Inhibitory Composition | Anti-Platelet Aggregation Activity (%) |
| --- | --- |
| A (Extraction with water only) | 92.7 |
| B (Ethyl Alcohol: 80%) | 94.6 |
| C (Ethyl Alcohol: 20%) | 95.5 |
| D (Ethyl Alcohol: 40%) | 97.1 |
| E (Ethyl Alcohol: 60%) | 93.7 |
| F (Ethyl Alcohol: 100%) | 96.3 |
| G (Ethyl Acetate: 60%) | 94.6 |
| H (Enzymatic Treatment) | 93.7 |

As shown in Table 7, all of the platelet aggregation inhibitory compositions exhibited high anti-platelet aggregation activities.

Example A'''-6

Preparation of Platelet Aggregation Inhibitory Composition-Containing Food (Tablet Type Sweet)

Five grams of the platelet aggregation inhibitory composition A obtained in Example A'''-1, 30 g of lactose, 12 g of DHA-containing powdery fat or oil (SUNCOAT DY-5, manufactured by Taiyo Kagaku Co., Ltd.), 4 g of a sucrose fatty acid ester, and 4 g of yogurt flavor were mixed, and this resulting mixture was subjected to pressure-molding using a rotary tableting machine to give platelet aggregation inhibitory composition-containing foodstuff (tablet type sweet), each tablet weighing 300 mg.

Example A'''-7

Preparation of Platelet Aggregation Inhibitory Composition-Containing Beverage

Five grams of the platelet aggregation inhibitory composition B obtained in Example A'''-2, 2.1 g of 1/5-concentrated grapefruit transparent juice, 30 g of erythritol, 2.5 g of citric acid crystals, 0.5 g of trisodium citrate, 0.5 g of L-ascorbic acid, 1.93 g of calcium lactate, 0.15 g of CCP, and 1.0 g of a grapefruit flavor were mixed and dissolved in water so as to make up a total volume of 1000 mL. The resulting mixture was filled into a 100 mL bottle, and the bottle was tightly sealed with a cap. Thereafter, the mixture was thermally sterilized at 90° C. for 30 minutes to give platelet aggregation inhibitory composition-containing foodstuff of the present invention.

Example A'''-8

Preparation of Platelet Aggregation Inhibitory Composition-Containing Beverage (Mixed Beverage of Vegetable and Fruit Juices)

To 100 mL of a commercially available mixed beverage of vegetable and fruit juices were added 0.2 g of the platelet aggregation inhibitory composition C obtained in Example A'''-2 and 3 g of a guar gum degradation product (SUNFIBER R; Taiyo Kagaku Co., Ltd.). The resulting mixture was mixed and dissolved to give platelet aggregation inhibitory composition-containing foodstuff (mixed beverage of vegetable and fruit juices) of the present invention.

Example A'''-9

Preparation of Platelet Aggregation Inhibitory Composition-Containing Cookies

Four grams of the platelet aggregation inhibitory composition D obtained in Example A'''-2 and 200 g of a commercially available cake mix powder were placed into a bowl, 35 g of butter was added thereto, and the contents were mixed with a wooden ladle. Twenty-five grams of beaten eggs were added thereto, and the resulting mixture was kneaded well until the dough was smooth. The dough was taken out on a table on which a wheat flour had been spread, and wheat flour was further spread over the dough. The dough was stretched with a rolling pin to a thickness of 5 mm. The dough was cut out with a round-shaped mold, and baked in an oven at 170° C. for 10 minutes to give platelet aggregation inhibitory composition-containing cookies of the present invention, each cookie weighing about 5 g.

Example A'''-10

Preparation of Platelet Aggregation Inhibitory Composition-Containing Yogurt

One gram of the platelet aggregation inhibitory composition H obtained in Example A'''-5, 95 g of a commercially available defatted milk (manufactured by Meiji Dairies Corporation, protein content 34%), and 35 g of commercially available salt-free butter (manufactured by Snow Brand Milk Products Co., Ltd.) were dissolved in 0.8 L of warm water. The mixture was mixed thoroughly, and adjusted to a total volume of 1 L. Thereafter, the resulting mixture was thermally sterilized at 90° C. for 15 minutes, cooled, inoculated with 3 g of a commercially available lactic acid bacteria starter (manufactured by Hansen) (2 g of *Streptococcus thermophilus* and 1 g of *Lactobacillus bulgaricus*). The mixture obtained was homogeneously mixed, and dispensed and filled into a 100-mL container, and the container was tightly sealed. The mixture was allowed to be fermented at 37° C. for 20 hours, and then cooled to give a platelet aggregation inhibitory composition-containing yogurt of the present invention.

Example A'''-11

Preparation of Platelet Aggregation Inhibitory Composition-Containing Orally Taken Liquid Food Fifty grams of sodium caseinate (manufactured by DMV), 42.5 g of an egg white enzymatically degraded product (manufactured by Taiyo Kagaku Co., Ltd.) and 100 g of dextrin (manufactured by Matsutani Chemical Industry Co., Ltd.) were dissolved in 1 L of water, to prepare an aqueous phase in a tank. Separately, 45 g of MCT (manufactured by Kao Corporation), 17.5 g of a palm oil (manufactured by Fuji Oil Co. Ltd.), 35 g of a safflower oil (manufactured by Taiyo Yushi K.K.), 0.7 g of lecithin (manufactured by Taiyo Kagaku Co., Ltd.) and 1 g of a defoaming agent (manufactured by Taiyo Kagaku Co., Ltd.) were mixed and dissolved, to prepare an oily phase. The oily phase was added to the aqueous phase in the tank, and the mixture was stirred and mixed, then warmed to 70° C. The mixture obtained was further homogenized with a homogenizer at a pressure of 14.7 MPa. Next, the resulting mixture was sterilized at 90° C. for 10 minutes, and concentrated, and the concentrate was spray-dried to give about 260 g of an intermediate product powder. Four grams of the platelet aggregation inhibitory composition C obtained in Example A'''-2, 156 g of dextrin (manufactured by Matsutani Chemical Industry Co., Ltd.), 18 g of a guar gum degradation product (SUNFIBER R; manufactured by Taiyo Kagaku Co., Ltd.), and small amounts of vitamins and minerals, and a powdery flavor were added to 200 g of the intermediate product powder. The mixture was homogeneously mixed to give about 380 g of an orally taken liquid food containing the platelet aggregation inhibitory composition.

Example A'''-12

Preparation of Platelet Aggregation Inhibitory Composition-Containing Tablet

Ten grams of the platelet aggregation inhibitory composition F obtained in Example A'''-3, 5 g of crystalline cellulose, 13.8 g of corn starch, 32.5 g of lactose, and 3.3 g of hydroxypropyl cellulose were mixed together, and the mixture was granulated. To the granulated product was added 1.0 g of magnesium stearate, and the resulting mixture was homogeneously mixed. This mixture obtained was subjected to pressure-molding using a rotary tableting machine to give a platelet aggregation inhibitory composition-containing tablet of the present invention, one tablet weighing 130 mg.

The similar compositions were prepared by substituting the platelet aggregation inhibitory compositions used in Examples A'''-6 to -12 with an antithrombotic composition, a fibrin formation inhibitory composition, an anti-platelet aggregation composition, a thrombus preventing composition, a composition for preventing thrombus, an extrinsic blood coagulation preventing composition, an anti-blood coagulant composition, a platelet aggregation preventing composition, a composition for preventing platelet aggregation, a composition for anti-thrombus, a composition for anti-platelet aggregation, a platelet aggregation thrombus inhibitory composition, a composition for inhibiting platelet aggregation thrombus, an antithrombotic agent, or a thrombus formation inhibitory agent of the present invention as shown in the following Examples.

Tea

Example B-1

Preparation 1 of Composition for Anti-Thrombus

Fifteen kilograms of hot water was added to 1 kg of green tea leaves, and the mixture was subjected to extraction at 90° C. for 30 minutes, and the mixture was filtered to remove the tea leaves. Thereafter, 12 kg of ethyl acetate was added to 12 kg of the filtrate, and the mixture was shaken, allowed to stand, and fractioned. The aqueous fraction was collected, and the solvent was removed under reduced pressure condition (0.067 mpa). Thereafter, the residue was spray-dried to give a composition for anti-thrombus A: 110 g of the present invention.

The resulting composition had a polyphenol content of 9.2%, and a caffeine content of 0.7%.

Test Example B-1

Confirmation of Antithrombotic Effect

The anti-coagulant activity of the composition for anti-thrombus of the present invention was assayed with a coagulometer (manufactured by SYSMEX CORPORATION) utilizing platelet poor plasma (PPP) separated from human blood.

Ten microliters of a sample, 25 microliters of an APTT reagent (manufactured by INTERNATIONAL REAGENTS CORPORATION), and 25 microliters of 10% cephalin were placed into a reaction cuvette to react the components at 37° C. for 3 minutes. Thereafter, 50 microliters of PPP was added thereto to react the components for 2 minutes. Finally, 50 microliters of 25 millimolar calcium chloride was added thereto to coagulate the mixture. A time period (seconds) by which the plasma was coagulated was measured, and defined as APTT.

At this time, water was added as the control, and the APTT was measured in the same manner. The anti-coagulant activity (%) was calculated from the APTT of the measured sample, relative to that of the control according to the following numerical formula.

Anti-Coagulant Activity(%)=(($APTT$ of Sample−$APTT$ of Control)/$APTT$ of Control)×100

In order to confirm the relationship between the concentration of the composition for anti-thrombus of the present invention and the anti-coagulant activity, the activity was assayed using the composition for anti-thrombus of the present invention of which amount was 0 (control), 1, 3 or 5 mg/mL calculated as a solid content concentration. The results are shown in Table 8 given below.

TABLE 8

| Concentration | APTT (seconds) | Anti-Coagulant Activity (%) |
|---|---|---|
| 0 mg/mL | 45 | 0 |
| 1 mg/mL | 47 | 4.4 |
| 3 mg/mL | 51 | 13.3 |
| 5 mg/mL | 56 | 40.0 |

It could be confirmed from the results of Table 8 mentioned above that the composition for anti-thrombus of the present invention exhibits a high anti-coagulant activity. In addition, it could be confirmed that the anti-coagulant activity increased proportionally to the increase of the concentration of the extract.

Example B-2

Preparation 2 of Composition for Anti-Thrombus

Two liters of water was added to 100 grams of the composition A for anti-thrombus obtained in Example B-1 to dissolve, and ethanol was added to the solution so as to make up a volume of 2.22 liters (final ethanol concentration: 20%). Thereafter, the mixture obtained was allowed to stand at room temperature for 24 hours to precipitate insoluble components. The precipitates were separated by centrifugation, dried under reduced pressure condition, and re-dissolved in 2 liters of water, and the mixture obtained was filtered to remove insoluble components. Thereafter, the filtrate was lyophilized to give of a composition for anti-thrombus B: 25 g (yield: 25%) of the present invention.

In the same manner, the compositions C, D and E for anti-thrombus of the present invention were obtained by adjusting the final ethanol concentrations to 40%, 60% and 80%, respectively.

The polyphenol contents in the compositions B to E for anti-thrombus obtained herein were B: 1.1%, C: 1.5%, D: 1.8% and E: 2.3%, respectively, and the caffeine contents were B: 0.1%, C: 0.3%, D: 0.4% and E: 0.5%, respectively.

Test Example B-2

Confirmation of Antithrombotic Effect

The APTT for the compositions B to E for anti-thrombus obtained in Example B-2 was measured in the same manner as in Test Example B-1 at a concentration of 5 mg/mL. The results are shown in Table 9.

TABLE 9

| Ethanol Concentration | APTT (seconds) | Anti-Coagulant Activity (%) |
|---|---|---|
| 20% | 96 | 113 |
| 40% | 104 | 131 |
| 60% | 85 | 89 |
| 80% | 84 | 87 |

It could be seen from the results of Table 9 mentioned above that the antithrombotic effect is the highest at an ethanol concentration of 40%.

Example B'-1

Preparation 1 of Composition for Anti-Platelet Aggregation

Fifteen kilograms of hot water was added to 1 kg of green tea leaves, and the mixture was subjected to extraction at 90° C. for 30 minutes, and the mixture was filtered to remove the tea leaves. Thereafter, 12 kg of ethyl acetate was added to 12 kg of the filtrate, and the mixture was shaken, allowed to stand, and fractioned. The aqueous fraction was collected, and the solvent was removed under reduced pressure condition (0.067 mpa). Thereafter, the residue was spray-dried to give a composition for anti-platelet aggregation A: 110 g of the present invention.

The resulting composition had a polyphenol content of 9.2%, and a caffeine content of 0.7%.

Test Example B'-1

Confirmation of Anti-Platelet Activity

The anti-platelet activity of the composition for anti-platelet aggregation of the present invention was obtained as follows: Eighty microliters of a sample was added to 400 µL of platelet rich plasma of a normal individual, 20 µL of ADP (1 mg/mL solution) was then added thereto as an aggregation-causing substance, and the platelet aggregation ratio after 5 minutes was determined by using a platelet aggregation analyzer (Aggregometer; manufactured by ISK).

Separately, water (sample concentration: 0 mg/mL) was added as the control, and the platelet aggregation ratio was determined in the same manner. The anti-platelet activity (%) was calculated from the determined platelet aggregation ratio, relative to that of the control according to the following numerical formula.

Anti-Platelet Activity(%)=((Platelet Aggregation Ratio of Control−Platelet Aggregation Ratio When Adding Sample)/Platelet Aggregation Ratio of Control)×100

The results determined at a sample concentration of 2.5, 5.0 or 7.5 mg/mL are shown in Table 10.

TABLE 10

| Sample Concentration | Anti-Platelet Activity (%) |
|---|---|
| 2.5 mg/mL | 13.4 |
| 5.0 mg/mL | 18.3 |
| 7.5 mg/mL | 32.9 |

It could be confirmed from the results of the above Table 10 that the anti-platelet aggregation composition of the present invention exhibits high anti-platelet activity. In addition, it was confirmed that the anti-platelet activity is increased proportionally to the increase in the concentration of the extract.

Example B'-2

Preparation 2 of Composition for Anti-Platelet Aggregation

Two hundreds milliliters of water was added to 10 grams of the composition A for anti-platelet aggregation obtained in Example B'-1 to dissolve, and ethanol was added thereto so as to make up a volume of 1 liter (final ethanol concentration: 80%). Thereafter, the resulting mixture was allowed to stand at room temperature for 24 hours to precipitate insoluble components.

The precipitates and the supernatant were separated by centrifugation. The precipitates were dried under reduced pressure condition, and re-dissolved in 200 milliliters of water, and the mixture was filtered to remove insoluble components. Thereafter, the filtrate was lyophilized, to give a composition for anti-platelet aggregation B: 2.7 g of the present invention, which is an 80% ethanol-insoluble fraction.

The supernatant was treated in the same manner, to give a composition for anti-platelet aggregation C: 7.3 g, which is an 80% ethanol-soluble fraction.

The compositions B and C for anti-platelet aggregation obtained in this example had polyphenol contents of B: 3.8% and C: 9.9%, respectively, and caffeine contents of B: 0.5% and C: 0.8%, respectively.

Test Example B'-2

Confirmation of Anti-Platelet Activity

The anti-platelet activities for the compositions B and C for anti-platelet aggregation obtained in Example B'-2 were assayed at a sample concentration of 5.0 mg/mL in the same manner as in Test Example B'-1. The results are shown in Table 11.

TABLE 11

| Sample | Anti-Platelet Activity (%) |
|---|---|
| Composition B for Anti-Platelet Aggregation (Ethanol-Precipitated Fraction) | 42.7 |
| Composition C for Anti-Platelet Aggregation (Ethanol-Soluble Fraction) | 29.7 |

It could be seen from the results of Table 11 mentioned above that the 80% ethanol-precipitated fraction has higher anti-platelet activity.

*Hibiscus*

Example C-1

Preparation 1 of Anti-Blood Coagulant Composition

Dry calyxes and petals of *hibiscus* were pulverized to a size of 40 mesh or smaller, and 3 L of distilled water was added to 150 g of the powder, and the mixture was subjected to extraction at 100° C. for 3 hours. Thereafter, the resulting mixture was centrifuged (8500 rpm, 10 minutes), and the supernatant was filtered to separate into the extract and the residue. The filtrate was concentrated under reduced pressure condition, and thereafter the concentrate was lyophilized to give an anti-blood coagulant composition A: 29.8 g (yield: 19.9%) of the present invention.

Example C-2

Preparation 2 of Anti-Blood Coagulant Composition

Dry leaves of *hibiscus* were pulverized to a size of 20 mesh or smaller, and 2 L of distilled water was added to 100 g of the powder, and the mixture was subjected to extraction at 100° C. for 3 hours. Thereafter, the resulting mixture was centrifuged (8500 rpm, 10 minutes), and the supernatant was filtered to separate into the extract and the residue. The filtrate was concentrated under reduced pressure condition, and thereafter the concentrate was lyophilized to give an anti-blood coagulant composition B: 13.4 g (yield: 13.4%) of the present invention.

Test Example C-1

Heparin-Like Activity

Ten microliters of heparin adjusted to a concentration of 0.05, 0.1, 0.2 or 0.4 U/mL and 40 µL of platelet poor plasma (PPP) separated from human blood were placed in a reaction cuvette, and the components were reacted at 37° C. for 1 minute. Thereafter, 50 µL of an APTT reagent (manufactured by INTERNATIONAL REAGENTS CORPORATION) was added thereto to further react at 37° C. for 2 minutes, and 50 µL of 25 mM calcium chloride was then added. The time period by which plasma was coagulated (APTT; second) was measured with a coagulometer (manufactured by SYSMEX CORPORATION). In order to evaluate the anti-blood coagulant effect of the anti-blood coagulant composition of the present invention, a calculation formula for the heparin-like activity value (U/mg) was obtained from the relationship between the heparin concentration and the APTT of heparin. The results are shown in Table 12 given below.

TABLE 12

| Heparin Concentration (U/mL) | APTT (seconds) |
|---|---|
| 0.05 | 39.6 |
| 0.1 | 50.9 |
| 0.2 | 86.4 |
| 0.4 | 180.2 |

From the results of Table 12, the relational formula for obtaining the heparin-like activity value was as follows:

$$\text{Heparin-Like Activity Value}(U/\text{mg}) = \frac{(0.2301 \times \text{Log}(APTT \text{ of Sample}) - 0.8053)}{\text{Sample Concentration(mg/mL)}}$$

Test Example C-2

Confirmation 1 of Anti-Blood Coagulant Effect

Ten microliters of a sample obtained by adjusting the amount of the anti-blood coagulant composition A obtained in Example C-1 and the anti-blood coagulant composition B obtained in Example C-2 so as to have a solid content concentration of 0, 0.1, 0.3, 0.5 or 1.0 mg/mL, respectively, and 40 μL of PPP were placed in a reaction cuvette to react the components at 37° C. for 1 minute. Thereafter, 50 μL of an APTT reagent (manufactured by INTERNATIONAL REAGENTS CORPORATION) was added to further react the components at 37° C. for 2 minutes. Thereafter, 50 μL of 25 mM calcium chloride was added to the reaction mixture, and the APTT was measured in the same manner as in Test Example C-1. The heparin-like activity value was obtained by the relational formula of the heparin-like activity value obtained in Test Example C-1. The results are shown in Table 13.

TABLE 13

| Item | Anti-Blood Coagulant Composition A | | Anti-Blood Coagulant Composition B | |
|---|---|---|---|---|
| Sample Concentration (mg/mL) | APTT (seconds) | Heparin-Like Activity Value (U/mg) | APTT (seconds) | Heparin-Like Activity Value (U/mg) |
| 0 | 28.0 | 0 | | |
| 0.1 | 36.3 | 0.21 | 34.5 | 0.09 |
| 0.3 | 45.1 | 0.24 | 36.8 | 0.10 |
| 0.5 | 53.4 | 0.22 | 41.1 | 0.08 |
| 1.0 | 89.7 | 0.23 | 48.3 | 0.09 |
| Average ± Standard Deviation | | 0.22 ± 0.01 | | 0.10 ± 0.01 |

It could be confirmed from the results of Table 13 that in the anti-blood coagulant compositions A and B of the present invention, the APTTs are increased as the concentration of the anti-blood coagulant composition is increased, that their heparin-like activity values as calculated in terms of heparin used as the anti-blood coagulating agent show average of 0.22 U/mg and 0.10 U/mg, respectively, and that high anti-blood coagulant effect is exhibited especially in a fruit portion.

Example C-3

Preparation 3 of Anti-Blood Coagulant Composition

Dry calyxes and petals of *hibiscus* were pulverized to a size of 40 mesh or smaller, and 3 L of distilled water was added to 150 g of the powder, and the mixture was subjected to extraction at 100° C. for 3 hours. Thereafter, the resulting mixture was centrifuged (8500 rpm, 10 minutes), and the supernatant was filtered to separate into the extract and the residue. The filtrate was concentrated under reduced pressure condition to a volume of 400 mL. Ethyl alcohol was added to the concentrate so as to make up a volume of 500 mL (final ethyl alcohol concentration: 20%). Thereafter, the mixture was allowed to stand at room temperature for 24 hours to precipitate insoluble components. The precipitates were separated by centrifugation (8500 rpm, 10 minutes). The supernatant was concentrated under reduced pressure condition, and 1 L of distilled water was added to the concentrate to re-dissolve. Thereafter, the mixture was filtered to remove insoluble components. The filtrate was concentrated under reduced pressure condition, and thereafter the concentrate was lyophilized to give a platelet aggregation preventing composition C: 12.4 g (yield: 8.3%) of the present invention. Ethyl alcohol was added to a concentrate obtained in the same manner so as to have a final ethyl alcohol concentration of 60% or 80% to precipitate insoluble components, and the same procedures were carried out to give platelet aggregation preventing compositions D: 9.8 g (yield: 6.5%) and E: 6.7 g (yield: 4.5%) of the present invention, respectively.

Test Example C-3

Confirmation 2 of Anti-Blood Coagulant Effect

The APTT was measured for the anti-blood coagulant compositions C, D and E obtained in Example C-3 at a concentration of 0.5 mg/mL in the same manner as in Test Example C-1. As a result, the APTT was 55.6 seconds, 63.7 seconds and 65.1 seconds, respectively, and the heparin-like activity value was 0.24 U/mg, 0.30 U/mg and 0.31 U/mg, respectively, whereby it could be confirmed that an even more enhanced anti-blood coagulant effect is exhibited by ethyl alcohol fractionation.

The APTT was measured for the precipitated component at a final ethyl alcohol concentration of 20% in Example C-3 in the same manner. As a result, the APTT was 38.1 seconds, and a heparin-like activity value was 0.06 U/mg, whereby it could be seen that the anti-blood coagulant fraction is contained in the ethyl alcohol-soluble fraction.

Example C'-1

Preparation 1 of Platelet Aggregation Preventing Composition

Dry calyxes and petal of *hibiscus* were pulverized to a size of 40 mesh or smaller, and 3 L of distilled water was added to 150 g of the powder, and the mixture was subjected to extraction at 100° C. for 3 hours. Thereafter, the resulting mixture was centrifuged (8500 rpm, 10 minutes), and the supernatant was filtered to separate into the extract and the residue. The filtrate was concentrated under reduced pressure condition, and thereafter the concentrate was lyophilized to give a platelet aggregation preventing composition A: 29.8 g (yield: 19.9%) of the present invention.

Example C'-2

Preparation 2 of Platelet Aggregation Preventing Composition

Dry leaves of *hibiscus* were pulverized to a size of 20 mesh or smaller, and 2 L of distilled water was added to 100 g of the powder, and the mixture was subjected to extraction at 100° C. for 3 hours. Thereafter, the resulting mixture was centrifuged (8500 rpm, 10 minutes), and the supernatant was filtered to separate into the extract and the residue. The filtrate was concentrated under reduced pressure condition, and thereafter the concentrate was lyophilized to give a platelet aggregation preventing composition B: 13.4 g (yield: 13.4%) of the present invention.

Test Example C'-1

Confirmation 1 of Anti-Platelet Aggregation Activity

The anti-platelet aggregation activity of the anti-platelet aggregation composition of the present invention was obtained as follows: To 200 μL of the blood of a normal individual was added 5 μL of a sample, 22 μL of ADP (manufactured by Sigma, 100 mg/vial) adjusted so as to give a final concentration of 10 μM was then added thereto as an aggregation-causing substance, and the platelet aggregation ratio after 5 minutes was determined by using a whole blood platelet aggregation analyzer (WBA-Neo, manufactured by ISK).

Separately, water (sample concentration 0 mg/mL) was added as the control, and the platelet aggregation ratio was determined in the same manner. The anti-platelet aggregation activity (%) was calculated from the determined platelet aggregation ratio, relative to that of the control according to the following numerical formula.

Anti-Platelet Aggregation Activity(%)=((Platelet Aggregation Ratio of Control−Platelet Aggregation Ratio When Adding Sample)/Platelet Aggregation Ratio of Control)×100

The determined results in which a sample was prepared by diluting the platelet aggregation preventing composition in distilled water so as to have a concentration of 1.25, 2.5 or 5.0 mg/mL are shown in Table 14.

TABLE 14

| Sample Concentration | Platelet Aggregation Preventing Composition A | Platelet Aggregation Preventing Composition B |
|---|---|---|
| 0 mg/mL | 0 | 0 |
| 1.25 mg/mL | 18.4 | 17.7 |
| 2.5 mg/mL | 43.9 | 40.3 |
| 5.0 mg/mL | 70.4 | 67.5 |

It was suggested from the results of the above Table 14 that the anti-platelet aggregation composition of the present invention has anti-platelet aggregation effect by inhibiting a stage of binding with other platelet due to GpIIb-IIIa associated with ADP via fibrinogen. In addition, it could be confirmed that the anti-platelet aggregation activity is increased proportionally to the increase in the concentration of the anti-platelet aggregation composition.

Example C'-3

Preparation 3 of Platelet Aggregation Preventing Composition

Dry calyxes and petals of *hibiscus* were pulverized to a size of 40 mesh or smaller, and 3 L of distilled water was added to 150 g of the powder, and the mixture was subjected to extraction at 100° C. for 3 hours. Thereafter, the resulting mixture was centrifuged (8500 rpm, 10 minutes), and the supernatant was filtered to separate the extract and the residue. The filtrate was concentrated under reduced pressure condition to a volume of 400 mL. Ethyl alcohol was added to the concentrate so as to make up a volume of 500 mL (final ethyl alcohol concentration: 20%). Thereafter, the mixture was allowed to stand at room temperature for 24 hours to precipitate insoluble components. The precipitates were separated by centrifugation (8500 rpm, 10 minutes). The supernatant was concentrated under reduced pressure condition, and thereafter 1 L of distilled water was added to the concentrate to re-dissolve. The mixture obtained was filtered to remove insoluble components. The filtrate was concentrated under reduced pressure condition, and the concentrate was lyophilized to give a platelet aggregation preventing composition C: 12.4 g (yield: 8.3%) of the present invention. Ethyl alcohol was added to a concentrate obtained in the same manner so as to have a final ethyl alcohol concentration of 60% or 80% to precipitate insoluble components, and the same procedures were carried out to give platelet aggregation preventing compositions D: 9.8 g (yield: 6.5%) and E: 6.7 g (yield: 4.5%) of the present invention, respectively.

Test Example C'-2

Confirmation 2 of Anti-Platelet Aggregation Activity

The platelet aggregation ratios were determined for the platelet aggregation preventing compositions C, D and E obtained in Example C'-3 at a concentration of 5.0 mg/mL in the same manner as in Test Example C'-1, and the anti-platelet aggregation activity was calculated. As a result, it could be confirmed that the anti-platelet aggregation activities (%) were 79.2, 81.4 and 83.6, respectively, showing that an even more enhanced anti-platelet aggregation effect is exhibited by the ethyl alcohol fractionation.

The platelet aggregation ratio was determined for the precipitated component at a final ethyl alcohol concentration of 20% in Example C'-3, and the anti-platelet aggregation activity was calculated in the same manner. As a result, the anti-platelet aggregation activity (%) was 11.9, whereby it could be seen that the anti-platelet aggregation is contained in the ethyl alcohol-soluble fraction.

Example C''-1

Preparation 1 of Composition for Preventing Platelet Aggregation

Dry calyxes and petals of *hibiscus* were pulverized to a size of 40 mesh or smaller, and 3 L of distilled water was added to 150 g of the powder, and the mixture was subjected to extraction at 100° C. for 3 hours. Thereafter, the resulting mixture was centrifuged (8500 rpm, 10 minutes), and the supernatant was filtered to separate into the extract and the residue. The filtrate was concentrated under reduced pressure condition, and thereafter the concentrate was lyophilized to give a composition for preventing platelet aggregation A: 29.8 g (yield: 19.9%) of the present invention.

Example C''-2

Preparation 2 of Composition for Preventing Platelet Aggregation

Dry leaves of *hibiscus* were pulverized to a size of 20 mesh or smaller, and 2 L of distilled water was added to 100 g of the powder, and the mixture was subjected to extraction at 100° C. for 3 hours. Thereafter, the resulting mixture was centrifuged (8500 rpm, 10 minutes), and the supernatant was filtered to separate into the extract and the residue. The filtrate was concentrated under reduced pressure condition, and thereafter the concentrate was lyophilized to give a composition for preventing platelet aggregation B: 13.4 g (yield: 13.4%) of the present invention.

Test Example C"-1

Confirmation 1 of Anti-Platelet Aggregation Activity

The anti-platelet aggregation activity of the anti-platelet aggregation composition of the present invention was obtained as follows: To 200 μL of the blood of a normal individual was added 5 μL of a sample, 22 μL of ristocetin sulfate (America Biochemical: 100 mg/vial) adjusted so as to have a final concentration 10 μM was then added as an aggregation-causing substance, and the platelet aggregation ratio after 5 minutes was determined by using a whole blood platelet aggregation analyzer (WBA-Neo, manufactured by ISK).

Separately, water (sample concentration: 0 mg/mL) was added as the control, and the platelet aggregation ratio was determined in the same manner. The anti-platelet aggregation activity (%) was calculated from the determined platelet aggregation ratio, relative to that of the control according the following numerical formula.

Anti-Platelet Aggregation Activity(%)=((Platelet Aggregation Ratio of Control−Platelet Aggregation Ratio When Adding Sample)/Platelet Aggregation Ratio of Control)×100

The determined results in which a sample was prepared by diluting the composition for preventing platelet aggregation with distilled water so as to have a concentration of 1.25, 2.5 or 5.0 mg/mL are shown in Table 15.

TABLE 15

| Sample Concentration | Composition A for Preventing Platelet Aggregation | Composition B for Preventing Platelet Aggregation |
| --- | --- | --- |
| 0 mg/mL | 0 | 0 |
| 1.25 mg/mL | 19.4 | 18.7 |
| 2.5 mg/mL | 43.9 | 45.3 |
| 5.0 mg/mL | 87.3 | 85.6 |

It was suggested from the results of the above Table 15 that the anti-platelet aggregation composition of the present invention has an anti-platelet aggregation effect by inhibiting formation of crosslinking between collagen and GpIb by vWF in the platelet aggregation. In addition, it was confirmed that the anti-platelet aggregation activity is increased proportionally to the increase in a concentration of the anti-platelet aggregation composition.

Example C"-3

Preparation 3 of Composition for Preventing Platelet Aggregation

Dry calyxes and petals of *hibiscus* were pulverized to a size of to 40 mesh or smaller, and 3 L of distilled water was added to 150 g of the powder, and the mixture was subjected to extraction at 100° C. for 3 hours. Thereafter, the resulting mixture was centrifuged (8500 rpm, 10 minutes), and the supernatant was filtered to separate into the extraction and the residue. The filtrate was concentrated under reduced pressure condition to a volume of 400 mL. Ethyl alcohol was added to the concentrate so as to make up a volume of 500 mL (final ethyl alcohol concentration: 20%). The mixture obtained was allowed to stand at room temperature for 24 hours to precipitate insoluble components. The precipitates were separated by centrifugation (8500 rpm, 10 minutes). The supernatant was concentrated under reduced pressure condition, and 1 L of distilled water was added to the concentrate to re-dissolve. Thereafter, the mixture was filtered to remove insoluble components. The filtrate was concentrated under reduced pressure condition, and thereafter the concentrate was lyophilized to give a composition for preventing platelet aggregation C: 12.4 g (yield: 8.3%) of the present invention. In addition, ethyl alcohol was added to a concentrate obtained in the same manner so as to have a final ethyl alcohol concentration of 60% or 80% to precipitate insoluble components, and the same procedures were carried out to give compositions for preventing platelet aggregation D: 9.8 g (yield: 6.5%) and E: 6.7 g (yield: 4.5%) of the present invention, respectively.

Test Example C"-2

Confirmation 2 of Anti-Platelet Aggregation Activity

The platelet aggregation ratios were determined for the compositions C, D and E for preventing platelet aggregation obtained in Example C"-3 at a concentration of 5.0 mg/mL in the same manner as in Test Example C"-1, and the anti-platelet aggregation activity was calculated. As a result, the anti-platelet aggregation activities (%) were 91.2, 93.4 and 94.6, respectively, whereby it could be confirmed that an even more enhanced anti-platelet aggregation effect is exhibited by the ethyl alcohol fractionation.

In addition, the platelet aggregation ratio was determined for the precipitated component at a final ethyl alcohol concentration of 20% in Example C"-3, and the anti-platelet aggregation activity was calculated in the same manner. As a result, the anti-platelet aggregation activity (%) was 13.7, whereby it could be seen that the anti-platelet aggregation is contained in the ethyl alcohol-soluble fraction.

Cocklebur

Example D-1

Preparation 1 of Platelet Aggregation Thrombus Inhibitory Composition

Dry calyxes and petals of cocklebur were pulverized to a size of 40 mesh or smaller, and 3 L of distilled water was added to 150 g of the powder, and the mixture was subjected to extraction at 100° C. for 3 hours. Thereafter, the resulting mixture was centrifuged (8500 rpm, 10 minutes), and the supernatant was filtered to separate into the extract and the residue. The filtrate was concentrated under reduced pressure condition, and thereafter the concentrate was lyophilized to give a platelet aggregation thrombus inhibitory composition A: 26.4 g (yield: 17.6%) of the present invention.

Example D-2

Preparation 2 of Platelet Aggregation Thrombus Inhibitory Composition

Dry seeds of cocklebur were pulverized to a size of 20 mesh or smaller, and 2 L of distilled water was added to 100 g of the powder, and the mixture was subjected to extraction at 100° C. for 3 hours. Thereafter, the resulting mixture was centrifuged (8500 rpm, 10 minutes), and the supernatant was filtered to separate into the extract and the residue. The filtrate was concentrated under reduced pressure condition, and thereafter the concentrate was lyophilized to give a platelet aggregation thrombus inhibitory composition B: 14.1 g (yield: 14.1%) of the present invention.

Test Example D-1

Confirmation 1 of Anti-Platelet Aggregation Activity

The anti-platelet aggregation activity of the anti-platelet aggregation composition of the present invention was obtained as follows: Five microliters of a sample was added to 200 μL of the blood of a normal individual, 22 μL of ADP (manufactured by Sigma: 100 mg/vial) adjusted so as to have a final concentration of 10 μM was then added thereto as an aggregation-causing substance, and the platelet aggregation ratio after 5 minutes was measured by using a whole blood platelet aggregation analyzer (WBA-Neo: manufactured by ISK).

Separately, water (sample concentration: 0 mg/mL) was used as the control, and the platelet aggregation ratio was determined in the same manner. The anti-platelet aggregation activity (%) was calculated from the measured platelet aggregation ratio, relative to that of the control according to the following numerical formula.

Anti-Platelet Aggregation Activity(%)=((Platelet Aggregation Ratio of Control−Platelet Aggregation Ratio When Adding Sample)/Platelet Aggregation Ratio of Control)×100

The determined results in which a sample was prepared by diluting the platelet aggregation thrombus inhibitory composition in distilled water so as to have a concentration of 1.25, 2.5 or 5.0 mg/mL are shown in Table 16.

TABLE 16

| Sample Concentration | Platelet Aggregation Thrombus Inhibitory Composition A | Platelet Aggregation Thrombus Inhibitory Composition B |
|---|---|---|
| 0 mg/mL | 0 | 0 |
| 1.25 mg/mL | 12.9 | 17.3 |
| 2.5 mg/mL | 33.5 | 37.6 |
| 5.0 mg/mL | 62.7 | 64.1 |

It was suggested from the results of Table 16 mentioned above that the platelet aggregation thrombus inhibitory composition of the present invention has an anti-platelet aggregation effect by inhibiting a stage of binding with other platelet due to GpIIb-IIIa associated with ADP via fibrinogen during the platelet aggregation. In addition, it could be confirmed that the anti-platelet aggregation activity is increased proportionally to the increase in the concentration of the platelet aggregation thrombus inhibitory composition.

Example D-3

Preparation 3 of Platelet Aggregation Thrombus Inhibitory Composition

Dry calyxes and petals of cocklebur were pulverized to a size of 40 mesh or smaller, and 3 L of distilled water was added to 150 g of the powder, and the mixture was subjected to extraction at 100° C. for 3 hours. Thereafter, the resulting mixture was centrifuged (8500 rpm, 10 minutes), and the supernatant was filtered to separate into the extract and the residue. The filtrate was concentrated under reduced pressure condition to a volume of 400 mL. Ethyl alcohol was added to the concentrate so as to make up a volume of 500 mL (final ethyl alcohol concentration: 20%). Thereafter, the mixture obtained was allowed to stand at room temperature for 24 hours to precipitate insoluble components. The precipitates were separated by centrifugation (8500 rpm, 10 minutes). The supernatant was concentrated under reduced pressure condition, and thereafter 1 L of distilled water was added to the concentrate to re-dissolve. Thereafter, the mixture obtained was filtered to remove insoluble components. The filtrate was concentrated under reduced pressure condition, and thereafter the concentrate was lyophilized to give a platelet aggregation thrombus inhibitory composition C: 11.4 g (yield: 7.6%) of the present invention. In addition, ethyl alcohol was added to a concentrate obtained in the same manner so as to have a final ethyl alcohol concentration of 60% or 80% to precipitate insoluble components, and the same procedures were carried out to give platelet aggregation preventing compositions D: 8.7 g (yield: 5.8%) and E: 5.9 g (yield: 3.9%) of the present invention, respectively.

Test Example D-2

Confirmation 2 of Anti-Platelet Aggregation Activity

The platelet aggregation ratios were determined for the platelet aggregation thrombus inhibitory compositions C, D and E obtained in Example D-3 at a concentration of 5.0 mg/mL in the same manner as in Test Example D-1, and the anti-platelet aggregation activities were calculated. As a result, the anti-platelet aggregation activities were 72.2(%), 74.6(%) and 76.4%, respectively, whereby it could be confirmed that an even more enhanced anti-platelet aggregation effect is exhibited by the ethyl alcohol fractionation.

In addition, the platelet aggregation ratio was determined for the precipitated component at a final ethyl alcohol concentration of 20% in Example D-3, and the anti-platelet aggregation activity was calculated in the same manner. As a result, the anti-platelet aggregation activity was 10.4(%), whereby it could be seen that the anti-platelet aggregation fraction is contained in the ethyl alcohol-soluble fraction.

Example D'-1

Preparation 1 of Composition for Inhibiting Platelet Aggregation Thrombus

Dry calyxes and petals of cocklebur were pulverized to a size of 40 mesh or smaller, and 3 L of distilled water was added to 150 g of the powder, and the mixture was subjected to extraction at 100° C. for 3 hours. Thereafter, the resulting mixture was centrifuged (8500 rpm, 10 minutes), and the supernatant was filtered to separate into the extract and the residue. The filtrate was concentrated under reduced pressure condition, and thereafter the concentrate was lyophilized to give a composition for inhibiting platelet aggregation thrombus A: 26.4 g (yield: 17.6%) of the present invention.

Example D'-2

Preparation 2 of Composition for Inhibiting Platelet Aggregation Thrombus

Dry seeds of cocklebur were pulverized to a size of 20 mesh or smaller, and 2 L of distilled water was added to 100 g of the powder, and the mixture was subjected to extraction at 100° C. for 3 hours. Thereafter, the resulting mixture was centrifuged (8500 rpm, 10 minutes), and the supernatant was filtered to separate into the extract and the residue. The filtrate was concentrated under reduced pressure condition, and thereafter the concentrate was lyophilized to give a composition for inhibiting platelet aggregation thrombus B: 14.1 g (yield: 14.1%) of the present invention.

Test Example D'-1

Confirmation 1 of Anti-Platelet Aggregation Activity

The anti-platelet aggregation activity of the composition for inhibiting platelet aggregation thrombus of the present invention was obtained as follows: Five microliters of a sample was added to 200 µL of the blood of a normal individual, 22 µL of ristocetin sulfate (American Biochemical, 100 mg/vial) adjusted so as to have a final concentration of 10 µM was then added thereto as an aggregation-causing substance, and the platelet aggregation ratio after 5 minutes was determined by using a whole blood platelet aggregation analyzer (WBA-Neo, manufactured by ISK).

Separately, water (sample concentration 0 mg/mL) was used as the control, and the platelet aggregation ratio was determined in the same manner. The anti-platelet aggregation activity (%) was calculated from the determined platelet aggregation ratio, relative to that of the control according to the following numerical formula.

Anti-Platelet Aggregation Activity(%)=((Platelet Aggregation Ratio of Control−Platelet Aggregation Ratio When Adding Sample)/Platelet Aggregation Ratio of Control)×100

The determined results in which a sample was prepared by diluting the composition for inhibiting platelet aggregation thrombus in distilled water so as to have a concentration of 1.25, 2.5 or 5.0 mg/mL are shown in Table 17.

TABLE 17

| Sample Concentration | Composition A for Inhibiting Platelet Aggregation Thrombus | Composition B for Inhibiting Platelet Aggregation Thrombus |
| --- | --- | --- |
| 0 mg/mL | 0 | 0 |
| 1.25 mg/mL | 17.6 | 19.2 |
| 2.5 mg/mL | 41.2 | 44.8 |
| 5.0 mg/mL | 83.7 | 86.7 |

It was suggested from the results of Table 17 mentioned above that the composition for inhibiting platelet aggregation thrombus of the present invention has an anti-platelet aggregation effect by inhibiting the cross-linking formation between collagen and GpIb via vWF during the platelet aggregation. In addition, it could be confirmed that the anti-platelet aggregation activity is increased proportionally to the increase in the concentration of the composition for inhibiting platelet aggregation thrombus.

Example D'-3

Preparation 3 of Composition for Inhibiting Platelet Aggregation Thrombus

Dry calyxes and petals of cocklebur were pulverized to a size of 40 mesh or smaller, and 3 L of distilled water was added to 150 g of the powder, and the mixture was subjected to extraction at 100° C. for 3 hours. Thereafter, the resulting mixture was centrifuged (8500 rpm, 10 minutes), and the supernatant was filtered to separate into the extract and the residue. The filtrate was concentrated under reduced pressure condition to a volume of 400 mL. Ethyl alcohol was added to the concentrate so as to make up a volume of 500 mL (final ethyl alcohol concentration: 20%). Thereafter, the mixture was allowed to stand at room temperature for 24 hours to precipitate insoluble components. The precipitates were separated by centrifugation (8500 rpm, 10 minutes). The supernatant was concentrated under reduced pressure condition, and 1 L of distilled water was added to the concentrate to re-dissolve. Thereafter, the mixture was filtered to remove insoluble components. The filtrate was concentrated under reduced pressure condition, and the concentrate was lyophilized to give a composition for inhibiting platelet aggregation thrombus C: 11.4 g (yield: 7.6%) of the present invention. In addition, ethyl alcohol was added to a concentrate obtained in the same manner so as to have a final ethyl alcohol concentration of 60% or 80% to precipitate insoluble components, and the same procedures were carried out to give platelet aggregation preventing compositions D: 8.7 g (yield: 5.8%) and E: 5.9 g (yield: 3.9%) of the present invention, respectively.

Test Example D'-2

Confirmation 2 of Anti-Platelet Aggregation Activity

The platelet aggregation ratios were determined for the compositions C, D and E for inhibiting platelet aggregation thrombus obtained in Example D'-3 at a concentration of 5.0 mg/mL in the same manner as in Test Example D'-1, and the anti-platelet aggregation activities were calculated. As a result, the anti-platelet aggregation activities (%) were 90.5, 91.3 and 93.4, respectively, whereby it could be confirmed that an even more enhanced anti-platelet aggregation effect is exhibited by the ethyl alcohol fractionation.

In addition, the platelet aggregation ratio was determined for the precipitated component at a final ethyl alcohol concentration of 20% in Example D'-3, and the anti-platelet aggregation activity was calculated in the same manner. As a result, the anti-platelet aggregation activity (%) was 9.8, whereby it could be seen that the anti-platelet aggregation is contained in the ethyl alcohol-soluble fraction.

*Gymnema*

Example E-1

Preparation 1 of Thrombus Formation Inhibitory Agent

A *gymnema* dry powder was pulverized to a size of 40 mesh or smaller, and 2 liters of distilled water was added to 80 grams of the powder, and the mixture was subjected to extraction at 55° C. for 3 hours. Thereafter, the resulting mixture was filtered to separate into the extract and the residue. Further, 2 liters of distilled water was added to the residue, and the mixture was subjected to extraction once again under the same conditions. Each of the extracts was combined, and thereafter the combined extract was lyophilized to give a thrombus formation inhibitory agent A: 28 g of the present invention.

Test Example E-1

Confirmation of Thrombus Formation Inhibitory Effect

The anti-platelet activity of the thrombus formation inhibitory agent of the present invention was obtained as follows: Eighty microliters of a sample was added to 400 µL of platelet rich plasma of a normal individual, 20 μL of ADP (1 mg/mL solution) was added then as an aggregation-causing substance, and the platelet aggregation ratio after 5 minutes was determined by using a platelet aggregation analyzer (Aggregometer, manufactured by ISK).

Separately, water (sample concentration: 0 mg/mL) was used as the control, and the platelet aggregation ratio was determined in the same manner. The anti-platelet activity (%) was calculated from the determined platelet aggregation ratio, relative to that of the control according to the following numerical formula.

Anti-Platelet Activity(%)=((Platelet Aggregation Ratio of Control−Platelet Aggregation Ratio When Adding Sample)/Platelet Aggregation Ratio of Control)×100

The determined results at a sample concentration of 2.5, 5.0 or 7.5 mg/mL are shown in Table 18.

TABLE 18

| Sample Concentration | Anti-Platelet Activity (%) |
|---|---|
| 2.5 mg/mL | 14.6 |
| 5.0 mg/mL | 18.3 |
| 7.5 mg/mL | 36.6 |

It could be confirmed from the results of Table 18 mentioned above that the thrombus formation inhibitory agent of the present invention exhibits a high anti-platelet activity. In addition, it could be confirmed that the anti-platelet activity is increased proportionally to the increase in the concentration of the extract.

Example E-2

Preparation 2 of Thrombus Formation Inhibitory Agent

A *gymnema* dry powder was pulverized to a size of 40 mesh or smaller, and 2 liters of distilled water was added to 80 g of the powder, and the mixture was subjected to extraction at 55° C. for 3 hours. Thereafter, the resulting mixture was filtered to separate into the extract and the residue. Further, 2 liters of distilled water was added to the residue, and the mixture was subjected to extraction once again under the same conditions. Each of the extracts was combined, and the combined extract was concentrated under reduced pressure condition to a volume of 200 milliliters. Ethanol was added to the concentrate so as to make up a volume of 1 liter (final ethanol concentration: 80%). Thereafter, the mixture was allowed to stand at 4° C. for 24 hours to precipitate insoluble components.

The precipitates and the supernatant were separated by centrifugation, and the precipitates were dried under reduced pressure condition. Thereafter, the residue was re-dissolved in 2 liters of water, and the mixture was filtered to remove insoluble components. Thereafter, the filtrate was lyophilized to give a thrombus formation inhibitory agent B: 7 g of the present invention, which is an 80% ethanol-insoluble fraction.

The supernatant was treated in the same manner to give a thrombus formation inhibitory agent C: 21 g, which is an 80% ethanol-soluble fraction.

Test Example E-2

Confirmation of Thrombus Formation Inhibitory Effect

The anti-platelet activities were determined for the thrombus formation inhibitory agents B and C obtained in Example E-2 at a sample concentration of 5.0 mg/mL in the same manner as in Test Example E-1. The results are shown in Table 19.

TABLE 19

| Sample | Anti-Platelet Activity (%) |
|---|---|
| Thrombus Formation Inhibitory Agent B (Ethanol-Precipitated Fraction) | 13.4 |
| Thrombus Formation Inhibitory Agent C (Ethanol-Soluble Fraction) | 47.6 |

It could be seen from the results of Table 19 mentioned above that the 80% ethanol-soluble fraction has a higher anti-platelet activity.

*Hizikia fusiforme*

Example F-1

Preparation 1 of Extrinsic Blood Coagulation Preventing Composition

Dry *Hizikia fusiforme* was pulverized to a size of 40 mesh or smaller, and 3 L of distilled water was added to 100 g of the powder, and the mixture was subjected to extraction at 100° C. for 3 hours. Thereafter, the resulting mixture was centrifuged (8500 rpm, 10 minutes), and the supernatant was filtered to separate into the extract and the residue. The filtrate was concentrated under reduced pressure condition, and thereafter the concentrate was lyophilized to give an extrinsic blood coagulation preventing composition A: 23.8 g (yield: 23.8%) of the present invention.

Test Example F-1

Confirmation 1 of Anti-Extrinsic Blood Coagulant Activity

The anti-extrinsic blood coagulant activity of the extrinsic blood coagulation preventing composition of the present invention was obtained as follows: Ten microliters of a sample of a heparin test solution adjusted by diluting standard heparin with distilled water so as to have a final concentration of 0, 0.05, 0.1, 0.2 or 0.3 U/mL was added to 40 μL of platelet rich plasma of a normal individual using a coagulometer (manufactured by SYSMEX CORPORATION) to react the components at 37° C. for 1 minute. Thereafter, 100 μL of a PT reagent (manufactured by INTERNATIONAL REAGENTS CORPORATION) was added thereto, and the time period by which plasma was coagulated was measured, i.e. PT was measured. From the relationship between the concentration of this heparin test solution and the PT, the following numerical formula for a heparin-like activity value (U/mg) was obtained.

$$\text{Heparin-Like Activity Value}(U/\text{mg}) = \frac{(2.0438 \times \text{Log}(PT \text{ of Sample}) - 4.8867)}{\text{Sample Concentration(mg/mL)}}$$

Thereafter, a sample was prepared by diluting the extrinsic blood coagulation preventing composition A of the present invention with distilled water so as to have a concentration of 0.078, 0.156, 0.313, 0.625 or 1.25 mg/mL calculated as a solid content. The PT was measured in the same manner and the resultant value was plugged into the above numerical formula to give a heparin-like activity value relative to heparin (1 U/mL) at each sample concentration.

In addition, a PT ratio was calculated at each sample concentration according to the following equation using a heparin test solution concentration of 0 mg/mL as the control.

PT Ratio=PT When Adding Sample/PT of Control
(Heparin Test Solution Concentration:0 mg/mL)

These results are shown in Table 20 and Table 21.

TABLE 20

Standard Heparin

| Heparin Concentration (U/mL) | PT (sec) |
|---|---|
| 1 | 18.1 |
| 0.5 | 13.2 |
| 0.25 | 12.3 |
| 0.125 | 11.8 |
| 0.0625 | 11.6 |
| 0 | 10.9 |

TABLE 21

Extrinsic Blood Coagulation Preventing Composition

| Sample Concentration (mg/mL) | PT (sec) | Heparin-Like Activity Value (U/mg) | PT Ratio |
|---|---|---|---|
| 1.25 | 34.5 | 1.88 | 3.17 |
| 0.625 | 18.3 | 1.69 | 1.68 |
| 0.313 | 14.9 | 2.03 | 1.37 |
| 0.156 | 12.4 | 1.66 | 1.14 |
| 0.078 | 11.6 | 1.57 | 1.06 |

It could be confirmed from the results of Table 21 that the extrinsic blood coagulation preventing composition A of the present invention has a high heparin-like activity value of 1.77 U/mg in average calculated in terms of heparin used as an anti-blood coagulant agent, and that PT and anti-extrinsic blood coagulant activity are also increased proportionally to the increase in the concentration of the extrinsic blood coagulation preventing composition.

Example F-2

Preparation 2 of Extrinsic Blood Coagulation Preventing Composition

Dry *Hizikia fusiforme* was pulverized to a size of 40 mesh or smaller, and 6 L of distilled water was added to 200 g of the powder, and the mixture was subjected to extraction at 100° C. for 3 hours. The resulting mixture was centrifuged (8500 rpm, 10 minutes), and the supernatant was filtered to separate into the extract and the residue. Thereafter, 6 L of distilled water was added to the residue, and the mixture was subjected to extraction once again under the same conditions. Each of the extracts was combined, and the combined extract was concentrated under reduced pressure condition to a volume of 400 mL. Ethyl alcohol was added to the concentrate so as to make up a volume of 500 mL (final ethyl alcohol concentration: 20%). Thereafter, the mixture was allowed to stand at room temperature for 24 hours to precipitate insoluble components. The precipitates were separated by centrifugation (8500 rpm, 10 minutes), and 1 L of distilled water was added to the precipitates to re-dissolve. The mixture obtained was filtered to remove insoluble components. The filtrate was concentrated under reduced pressure condition, and the concentrate was lyophilized to give an extrinsic blood coagulation preventing composition B: 32.8 g (yield: 16.4%) of the present invention. In addition, ethyl alcohol was added to the concentrate obtained in the same manner so as to have a final ethyl alcohol concentration of 60% or 80% to precipitate the insoluble components, and the same procedures were carried out to give extrinsic blood coagulation preventing compositions C: 28.4 g (yield: 14.2%) and D: 21.2 g (yield: 10.6%) of the present invention, respectively. In addition, ethyl alcohol was added to the supernatant having a final ethyl alcohol concentration of 60% so as to have an ethyl alcohol final concentration of 80%, to give precipitates, and the same procedures were carried out, to give an extrinsic blood coagulation preventing composition E: 2.8 g (yield: 1.4%) of the present invention.

Example F-3

Preparation 3 of Extrinsic Blood Coagulation Preventing Composition

Dry *Hizikia fusiforme* was pulverized to a size of 40 mesh or smaller, and 3 L of 50% of ethyl alcohol in water was added to 100 g of the powder. The mixture was allowed to stand at room temperature for 3 days, and the mixture was subjected to extraction. Thereafter, the resulting mixture was centrifuged (8500 rpm, 10 minutes), and the supernatant was filtered to separate into the extract and the residue. The filtrate was concentrated under reduced pressure condition, and thereafter the concentrate was lyophilized to give an extrinsic blood coagulation preventing composition F: 21.1 g (yield: 21.1%) of the present invention.

Test Example F-2

Confirmation 2 of Anti-Extrinsic Blood Coagulant Activity

The PTs were determined for the extrinsic blood coagulation preventing composition A obtained in Example F-1, the extrinsic blood coagulation preventing compositions B, C, D and E obtained in Example F-2, and the extrinsic blood coagulation preventing composition F obtained in Example F-3 at a concentration of 0.2 mg/mL calculated as a solid content. Thereafter, the resultant value was plugged into the calculation formula for a heparin-like activity value (U/mg) in Test Example F-1, and the heparin-like activity value and the PT ratio of each extrinsic blood coagulation preventing composition were obtained. In addition, a sample was prepared using the supernatant fraction with 80% ethyl alcohol in Example F-2 in the same manner, and the heparin-like activity value and the PT ratio were obtained. The results are shown in Table 22.

TABLE 22

| | PT (sec) | Heparin-Like Activity Value (U/mg) | PT Ratio |
|---|---|---|---|
| Extrinsic Blood Coagulation Preventing Composition A | 13.3 | 2.01 | 1.22 |
| Extrinsic Blood Coagulation Preventing Composition B | 15.5 | 3.58 | 1.42 |
| Extrinsic Blood Coagulation Preventing Composition C | 16.8 | 4.4 | 1.54 |
| Extrinsic Blood Coagulation Preventing Composition D | 17.6 | 4.87 | 1.61 |

TABLE 22-continued

|  | PT (sec) | Heparin-Like Activity Value (U/mg) | PT Ratio |
|---|---|---|---|
| Extrinsic Blood Coagulation Preventing Composition E | 18.8 | 5.55 | 1.72 |
| Extrinsic Blood Coagulation Preventing Composition F | 15.8 | 3.77 | 1.45 |
| 80% Ethyl Alcohol Supernatant Fraction | 11.1 | 0.16 | 1.02 |

It could be confirmed from Table 22 that the ethyl alcohol-precipitated components obtained in Example F-2 exhibit high heparin-like activity values. It could be seen that an excellent anti-extrinsic blood coagulant effect is exhibited in the ethyl alcohol-precipitated portion.

Example F'-1

Preparation 1 of Thrombus Preventing Composition

Dry *Hizikia fusiforme* was pulverized to a size of 40 mesh or smaller, and 3 L of distilled water was added to 100 g of the powder, and the mixture was subjected to extraction at 100° C. for 3 hours. Thereafter, the resulting mixture was centrifuged (8500 rpm, 10 minutes), and the supernatant was filtered to separate into the extract and the residue. The filtrate was concentrated under reduced pressure condition, and thereafter the concentrate was lyophilized to give a thrombus preventing composition A: 23.8 g of the present invention. Its yield was 23.8%.

Test Example F'-1

Confirmation of Thrombus Preventing Effect

The thrombus preventing effect of the thrombus preventing composition A of the present invention was evaluated by measuring the APTT with the coagulometer utilizing platelet poor plasma (PPP) separated from human blood.

Ten microliters of a sample of which amount was adjusted so as to have a concentration of the thrombus preventing composition A of the present invention of 0.075, 0.15, 0.3 or 0.5 mg/mL calculated as a solid content, and 40 µL of PPP were placed in a reaction cuvette to react the components at 37° C. for 1 minute. Thereafter, 50 µL of an APTT reagent (manufactured by INTERNATIONAL REAGENTS CORPORATION) was added to further react the components at 37° C. for 2 minutes, and 50 µL of 25 mM calcium chloride was then added thereto. The time period (seconds) by which plasma was coagulated was measured, and defined as APTT. The results are shown in Table 23 given below.

Here, as the control, APTT was measured using heparin adjusted to have a concentration of 0.05, 0.1, 0.2 and 0.3 U/mL as a sample in the same manner. The following calculation formula for a heparin-like activity value (U/mg) was obtained from this relationship between the concentration of this heparin and APTT of heparin, and the resultant value was plugged into this calculation formula to give a heparin-like activity value relative to heparin (1 U/mL) at each sample concentration. The results are shown in Table 24 shown below.

$$\text{Heparin-Like Activity Value}(U/\text{mg}) = \frac{(0.1648 \times \text{Log}(APTT \text{ of Sample}))}{\text{Sample Concentration(mg/mL)}}$$

TABLE 23

| Heparin Concentration (U/mL) | APTT (second) |
|---|---|
| 0.05 | 39.6 |
| 0.1 | 50.9 |
| 0.2 | 86.4 |
| 0.3 | 180.2 |

TABLE 24

| Sample Concentration (mg/mL) | APTT (second) | Heparin-Like Activity Value (U/mg) |
|---|---|---|
| 0.075 | 33.1 | 0.37 |
| 0.15 | 38.3 | 0.35 |
| 0.3 | 53.4 | 0.36 |
| 0.5 | 84.2 | 0.36 |
|  | Average | 0.36 |

It could be confirmed from the results of Table 24 that the APTT in the thrombus preventing composition A of the present invention increased together with the increase in the concentration of the thrombus preventing composition, and that the heparin-like activity values calculated in terms of heparin used as the anti-blood coagulant agent had an average of 0.36 U/mg, whereby exhibiting a high anti-blood coagulant effect.

Example F'-2

Preparation 2 of Thrombus Preventing Composition

Dry *Hizikia fusiforme* was pulverized to a size of 40 mesh or smaller, and 6 L of distilled water was added to 200 g of the powder, and the mixture was subjected to extraction at 100° C. for 3 hours. The resulting mixture was centrifuged (8500 rpm, 10 minutes), and the supernatant was filtered to separate into the extract and the residue. Thereafter, 6 L of distilled water was added to the residue, and the mixture was subjected to extraction once again under the same conditions. Each of the extracts was combined, and the combined extract was concentrated under reduced pressure condition to a volume of 400 mL. Ethanol was added to the concentrate so as to make up a volume of 500 mL (final ethanol concentration: 20%). Thereafter, the mixture obtained was allowed to stand at room temperature for 24 hours to precipitate insoluble components. The precipitates were separated by centrifugation (8500 rpm, 10 minutes), 1 L of distilled water was added to the precipitates to re-dissolve, and the mixture was filtered to remove insoluble components. The filtrate was concentrated under reduced pressure condition, and the concentrate was lyophilized to give a thrombus preventing composition B: 16.4 g of the present invention. In addition, ethanol was added to a concentrate obtained in the same manner so as to have a final ethanol concentration of 60% or 80% to precipitate insoluble components, and the same procedures were carried out, to give thrombus preventing compositions C: 21.4 g and D: 25.2 g of the present invention. In addition, ethanol was added to the supernatant having a final ethanol concentration of 60% so as to give a final ethanol concentration of 80%, to give precipitates, and the same procedures were carried out, to give a thrombus preventing composition E: 2.8 g of the present invention.

Example F'-3

Preparation 3 of Thrombus Preventing Composition

Dry *Hizikia fusiforme* was pulverized to a size of 40 mesh or smaller, and 3 L of 50% ethanol in water was added to 100 g of the powder. The mixture was allowed to stand at room temperature for 3 days, and the mixture was subjected to extraction. Thereafter, the resulting mixture was centrifuged (8500 rpm, 10 minutes), and the supernatant was filtered to separate into the extract and the residue. The filtrate was concentrated under reduced pressure condition, and thereafter the concentrate was lyophilized to give a thrombus preventing composition F: 21.1 g of the present invention. Its yield was 21.1%.

Test Example F'-2

Confirmation of Thrombus Preventing Effect

The APTTs were measured for the thrombus preventing composition A obtained in Example F'-1, the thrombus preventing compositions B, D and E obtained in Example F'-2, and the thrombus preventing composition F obtained in Example F'-3 at a concentration of 0.2 mg/mL calculated as a solid content in the same manner as in Test Example F'-1. Thereafter, the resultant value was plugged into the calculation formula for the heparin-like activity value (U/mg) in Test Example F'-1 to give a heparin-like activity value of each thrombus preventing composition. In addition, a sample was prepared in the same manner for the supernatant fraction with 80% ethanol in Example F'-2, and its heparin-like activity value was obtained. The results are shown in Table 25.

TABLE 25

| | APTT (second) | Heparin-Like Activity Value (U/mg) |
|---|---|---|
| Thrombus Preventing Composition A | 43.2 | 0.36 |
| Thrombus Preventing Composition B | 121.6 | 1.21 |
| Thrombus Preventing Composition C | 189.7 | 1.58 |
| Thrombus Preventing Composition D | 178.5 | 1.53 |
| Thrombus Preventing Composition E | 195.8 | 1.60 |
| Thrombus Preventing Composition F | 137.4 | 1.31 |
| 80% Ethanol Supernatant Fraction | 30.9 | 0.08 |

It could be confirmed from Table 25 that the ethanol-precipitated components obtained in Example F'-2 showed a high heparin-like activity value, whereby it could be seen that an excellent anti-blood coagulant effect is found in the ethanol-precipitated portion of the water extract.

Example F''-1

Preparation 1 of Composition for Preventing Thrombus

Dry *Hizikia fusiforme* was pulverized to a size of 40 mesh or smaller, 3 L of distilled water was added to 100 g of the powder, and 0.1 g of protease was further added thereto, and the mixture was subjected to extraction at 55° C. for 3 hours. The enzyme was then deactivated at 90° C. for 30 minutes. Thereafter, the resulting mixture was centrifuged (8500 rpm, 10 minutes). The supernatant was filtered, and the filtrate was spray-dried to give a composition for preventing thrombus A: 29.4 g of the present invention. Its yield was 29.4%.

Test Example F'''-1

Confirmation of Thrombus Preventing Effect

The thrombus preventing effect of the composition A for preventing thrombus of the present invention was evaluated by measuring the APTT with a coagulometer (manufactured by SYSMEX CORPORATION) utilizing platelet poor plasma (PPP) separated from human blood.

Ten microliters of a sample of which amount was adjusted so as to have a concentration of 0.075, 0.15, 0.3 or 0.5 mg/mL calculated as a solid content, and 40 µl of PPP were placed in a reaction cuvette to react the components at 37° C. for 1 minute. Thereafter, 50 µL of an APTT reagent (manufactured by INTERNATIONAL REAGENTS CORPORATION) was added thereto to further react the components at 37° C. for 2 minutes, and 50 µL of 25 mM calcium chloride was then added thereto. The time period (second) by which plasma was coagulated was measured, and defined as APTT. The results are shown in Table 26 given below.

Here, as the control, the APTT was measured in the same manner using heparin adjusted to a concentration of 0.05, 0.1, 0.2 or 0.3 U/mL as a sample. The following calculation formula for a heparin-like activity value (U/mg) was obtained from the relationship between the concentration of heparin and the APTT of heparin. The resultant value was plugged into the calculation formula to give a heparin-like activity value relative to heparin (1 U/mL) at each sample concentration. The results are shown in Table 27 given below.

$$\text{Heparin-Like Activity Value}(U/\text{mg}) = \frac{(0.1648 \times \text{Ln}(APTT \text{ of Sample}) - 0.5487)}{\text{Sample Concentration(mg/mL)}}$$

TABLE 26

| Heparin Concentration (U/mL) | APTT (second) |
|---|---|
| 0.05 | 39.6 |
| 0.1 | 50.9 |
| 0.2 | 86.4 |
| 0.3 | 180.2 |

TABLE 27

| Concentration (mg/mL) of Composition A for Preventing Thrombus | APTT (second) | Heparin-Like Activity Value (U/mg) |
|---|---|---|
| 0.075 | 35.4 | 0.52 |
| 0.15 | 44.3 | 0.51 |
| 0.3 | 72.6 | 0.53 |
| 0.5 | 133.2 | 0.51 |
| | Average | 0.52 |

It could be confirmed from the results of Table 27 that the APTT in the composition A for preventing thrombus of the present invention increased together with the increase in the concentration of the composition for preventing thrombus, and that a heparin-like activity value calculated in terms of heparin used as an anti-blood coagulant agent has an average of 0.52 U/mg, whereby exhibiting a high anti-blood coagulant effect.

Example F'''-2

Preparation 2 of Composition for Preventing Thrombus

Dry *Hizikia fusiforme* was pulverized to a size of 40 mesh or smaller, 3 L of distilled water was added to 100 g of the powder, and 0.1 g of a protease was further added thereto, and the mixture was subjected to extraction at 55° C. for 3 hour. The enzyme was then deactivated at 90° C. for 30 minutes. Thereafter, the resulting mixture was centrifuged (8500 rpm, 10 minutes). The supernatant was filtered, and the filtrate was concentrated under reduced pressure condition to a volume of 200 mL. Ethanol was added to the concentrate so as to make up a volume of 250 mL (final ethanol concentration: 20%), and thereafter the mixture was allowed to stand at room temperature for 24 hours to precipitate insoluble components. The resulting mixture was centrifuged (8500 rpm, 10 minutes) to separate precipitates, 1 L of distilled water was added to the precipitates to re-dissolve, and the mixture obtained was filtered to remove insoluble components. The filtrate was concentrated under reduced pressure condition, and the concentrate was lyophilized to give a composition for preventing thrombus B: 24.5 g of the present invention. In addition, ethanol was added to the concentrate obtained in the same manner so as to have a final ethanol concentration of 60% to precipitate insoluble components, and the same procedures were carried out, to give a composition for preventing thrombus C: 21.4 g of the present invention.

Comparative Example F'''-1

Preparation of Comparative Composition

Dry *Hizikia fusiforme* was pulverized to a size of 40 mesh or smaller, and 3 L of distilled water was added to 100 g of the powder, and the mixture was subjected to extraction at 100° C. for 3 hours. Thereafter, the resulting mixture was centrifuged (8500 rpm, 10 minutes), and the supernatant was filtered to separate into the extract and the residue. The filtrate was concentrated under reduced pressure condition, and thereafter the concentrate was lyophilized to give a comparative composition: 23.8 g.

Test Example F'''-2

Confirmation of Thrombus Preventing Effect

The APTTs were measured for the composition A for preventing thrombus obtained in Example F'''-1, the compositions B and C for preventing thrombus obtained in Example F'''-2, and the comparative composition obtained in Comparative Example F'''-1 in the same manner as in Test Example F'''-1 at a concentration of 0.2 mg/mL calculated as a solid content. Thereafter, the resultant value was plugged into the calculation formula for a heparin-like activity value (U/mg) in Test Example F'''-1, to give a heparin-like activity value of each composition for preventing thrombus. The results are shown in Table 28.

TABLE 28

| Concentration (mg/mL) of Composition A for Preventing Thrombus | APTT (second) | Heparin-Like Activity Value (U/mg) |
|---|---|---|
| 0.075 | 35.4 | 0.52 |
| 0.15 | 44.3 | 0.51 |
| 0.3 | 72.6 | 0.53 |
| 0.5 | 133.2 | 0.51 |
| | Average | 0.52 |

It could be confirmed from Table 28 that an even more enhanced heparin-like activity value is exhibited by subjecting the water extract of *Hizikia fusiforme* to an enzyme treatment, and further subjected to an alcohol fractionation treatment.

Carrageenan

Example G-1

Preparation 1 of Antithrombotic Agent

Ten grams of commercially available ι-carrageenan (Suncara No. 208; manufactured by Taiyo Kagaku Co., Ltd.) was dissolved in 1 liter of hot water at 80° C. Thereafter, the resulting mixture was filtered, the filtrate was concentrated under reduced pressure condition, and the concentrate was lyophilized to give an antithrombotic agent A of the present invention.

In the same manner, κ-carrageenan (Suncara No. 1572; manufactured by Taiyo Kagaku Co., Ltd.) or λ-carrageenan (Suncara No. 1057; manufactured by Taiyo Kagaku Co., Ltd.) was used to give an antithrombotic agent B or C of the present invention.

Test Example G-1

Confirmation of Antithrombotic Effect

The anti-coagulant activity of the antithrombotic agent of the present invention was assayed with a coagulometer (manufactured by SYSMEX CORPORATION) utilizing platelet poor plasma (PPP) separated from human blood.

Ten microliters of a sample, 25 microliters of an APTT reagent (manufactured by INTERNATIONAL REAGENTS CORPORATION), and 25 microliters of 10% cephalin were placed into a reaction cuvette to react the components at 37° C. for 3 minutes, and 50 microliters of PPP was placed in the reaction cuvette to react the components for 2 minutes. Finally, 50 microliters of 25 millimolar calcium chloride was added to coagulate the mixture obtained. The time period (second) by which plasma was coagulated was measured, and defined as APTT.

Here, water was used as the control, and the APTT was measured in the same manner. The anti-coagulant activity (%) was calculated from the measured APTT of the sample, relative to that of the control according to the following numerical formula.

Anti-Coagulant Activity(%)=((*APTT* of Sample−*APTT* of Control)/*APTT* of Control)×100

In order to confirm the relationship between the concentration of the antithrombotic agent of the present invention and the anti-coagulant activity, the activities were assayed by using the antithrombotic agent of the present invention having a concentration of 0 (control), 1, 3 or 5 mg/mL calculated as a solid content. The results are shown in Table 29 given below.

TABLE 29

| Sample | Concentration | APTT (sec) | Anti-Coagulant Activity (%) |
| --- | --- | --- | --- |
|  | 0 mg/mL | 45 | 0 |
| Antithrombotic | 0.5 mg/mL | 162 | 260 |
| Composition A | 2.5 mg/mL | 600 or more | 1200 or more |
| (ι-carrageenan) | 5.0 mg/mL | 600 or more | 1200 or more |
| Antithrombotic | 0.5 mg/mL | 99 | 120 |
| Composition B | 2.5 mg/mL | 491 | 991 |
| (κ-carrageenan) | 5.0 mg/mL | 600 or more | 1200 or more |
| Antithrombotic | 0.5 mg/mL | 398 | 784 |
| Composition C | 2.5 mg/mL | 600 or more | 1200 or more |
| (λ-carrageenan) | 5.0 mg/mL | 600 or more | 1200 or more |

It could be confirmed from the results of Table 29 given above that the antithrombotic agent of the present invention exhibits a high anti-coagulant activity. In addition, it could be confirmed that the anti-coagulant activity increased proportionally to the increase in the concentration of the extract.

INDUSTRIAL APPLICABILITY

According to the present invention, there is provided a composition for inhibiting thrombus formation, comprising a given plant component having a thrombus formation inhibitory activity. The composition for inhibiting thrombus formation of the present invention can be applied to, for instance, foodstuff, quasi-drugs, medicaments and feeds.

The invention claimed is:

1. A method for inhibiting fibrin formation comprising administering a composition comprising an extract of dried amla fruit to an individual in need thereof.

2. The method of claim 1, wherein the administering step comprises the individual ingesting the composition.

3. The method of claim 2, wherein the composition is in the form of a food, a drink, an animal feed, a quasi-drug, or a medicament.

4. The method of claim 2, wherein the composition is in the form of a cookie, a yoghurt, or a tablet.

5. The method of claim 1, wherein the extract of dried amla fruit is capable of being essentially completely dissolved by an aqueous solution comprising 20% to 80% ethanol.

6. The method of claim 1, wherein the extract of dried amla fruit is capable of being essentially completely dissolved in an aqueous solution comprising 60% to 80% ethanol.

7. The method of claim 1, further comprising preparing the extract of dried amla fruit by performing a solvent extraction of pulverized dried amla fruit to produce a solvent extract.

8. The method of claim 7, wherein the solvent extraction is performed with at least one solvent selected from water, a hydrochloric acid solution, a sulfuric acid solution, a sodium hydroxide solution, a potassium hydroxide solution, methanol, ethanol, n-propyl alcohol, isopropyl alcohol, butyl alcohol, ethyl acetate, butyl acetate, diethyl ether, methyl ether, methyl isobutyl ketone, hexane, chloroform, and acetone.

9. The method of claim 8, wherein the solvent is removed from the solvent extract by lyophilization, thereby producing a lyophilization residue.

10. The method of claim 9, wherein the composition is in the form of a cookie, a yoghurt, or a tablet containing the lyophilization residue.

11. The method of claim 9, wherein the lyophilization residue is further solvent extracted.

12. The method of claim 7, wherein the solvent extraction is performed with at least one of water and a solution of water and ethanol.

13. The method of claim 7, wherein the pulverized dried amla fruit has a particle size of 40 mesh or smaller.

14. The method of claim 7, wherein the solvent extract is further purified using at least one of chromatography, centrifugation, precipitation, and filtration.

* * * * *